(12) United States Patent
Bolduc et al.

(10) Patent No.: US 10,107,756 B2
(45) Date of Patent: Oct. 23, 2018

(54) FLUORESCENCE ASSAY FOR QUANTIFICATION OF PICOLINATE AND OTHER COMPOUNDS IN OXIDIZERS AND OXIDIZING COMPOSITIONS

(71) Applicant: Ecolab USA, Inc., Saint Paul, MN (US)

(72) Inventors: John Wilhelm Bolduc, Inver Grove Heights, MN (US); Eugene Tokhtuev, Duluth, MN (US); Anatoly Skirda, Hermantown, MN (US); Anna Pilipchenko, Duluth, MN (US); Justin Scott Valenstein, Eagan, MN (US); Amanda Bakken, Eagan, MN (US); Stacy Fawbush, St. Paul, MN (US); Jeffrey S. Hutchison, Minneapolis, MN (US)

(73) Assignee: Ecolab USA Inc., Saint Paul, MN (US)

(*) Notice: Subject to any disclaimer, the term of this patent is extended or adjusted under 35 U.S.C. 154(b) by 235 days.

(21) Appl. No.: 14/993,960

(22) Filed: Jan. 12, 2016

(65) Prior Publication Data
US 2017/0199124 A1 Jul. 13, 2017

(51) Int. Cl.
*G01N 21/00* (2006.01)
*G01N 21/64* (2006.01)

(52) U.S. Cl.
CPC ..... *G01N 21/645* (2013.01); *G01N 2201/061* (2013.01)

(58) Field of Classification Search
CPC .................................................. G01N 21/645
USPC ............................................................ 436/82
See application file for complete search history.

(56) References Cited

U.S. PATENT DOCUMENTS

| 7,306,930 B2 | 12/2007 | Ponce et al. | |
| 2009/0127207 A1* | 5/2009 | Okamoto | B63B 13/00 210/747.6 |
| 2014/0097144 A1 | 4/2014 | Li et al. | |

OTHER PUBLICATIONS

Despotovic et al. "Fluorescent Assay for Directed Evolution of Perhydrolases" Journal of Biomolecular Screening 17(6) 796-805 2012 (Year: 2012).*
Odo et al. Fluorescent Derivatization of Aromatic Carboxylic Acids with Horseradish Peroxidase in the Presence of Excess Hydrogen Peroxide Analytical Sciences Jan. 2015, vol. 31 (Year: 2015).*

(Continued)

*Primary Examiner* — Christine T Mui
*Assistant Examiner* — Emily R. Berkeley
(74) *Attorney, Agent, or Firm* — McKee, Voorhees & Sease, PLC

(57) ABSTRACT

A method of fluorometrically detecting the concentration of chemical components in oxidizing formulations is disclosed. In a particular embodiment the detection is of the stabilizing component of picolinic acid, present in such formulations, although any component which fluoresces may be detected. According to the invention sample preparation of the oxidizing formulation includes adding to said sample an excess of reducing agent to bind peracid, and in the case of picolinic acid, adding to said sample an excess of terbium chloride. The sample then is subjected to radiation to induce fluorescence and the concentration of said chemical component is determined by a linear relationship between fluorescence emitted and the concentration of the target chemical.

27 Claims, 10 Drawing Sheets

(56) References Cited

OTHER PUBLICATIONS

Hindle, Alistair A. et al., "Dipiconlinic acid (DPA) assay revisited and appraised for spore detection", The Analyist, (1999), 124, pp. 1599-1604.

Smith, Clint B., et al., "In Situ Surface-Etched Bacterial Spore Detection Using Dipicolinic Acid-Europium-Silica Nanoparticle Bireporters", Applied Spectroscopy, (2011), vol. 65, No. 8, pp. 866-875.

"Hydrogen Peroxide, POAA, Octanoic Acid, POOA and HEDP as Components of Antimicrobial Washing Solution", Chemical and Technical Assessment, Prepared by Ma. Patricia V. Azanza, 2004, pp. 1-7 2004.

Despotovic, Dragana, et al., "Fluorescent Assay for Directed Evolution of Perhydrolases", Journal of Biomolecular Screening, pp. 1-10 Jan. 17, 2012 Jan. 17, 2012.

Jacks, Thomas J., "Spectrofluorometric Determination of Hypohalites and Peroxyacids Using Kojic Acid", published online: Oct. 25, 2011, http:/www.tandfonline.com/doi/abs/10.1081/AL-120034062, 2 pages, accessed on Nov. 8, 2017 Oct. 25, 2011.

de Oliveira, Moacir et al., "A new spectrophotometric method to detect residual amounts of peroxide after reprocessing hemodialysis filters", Health Economics and Management, pp. 70-74, Feb. 8, 2011 Feb. 8, 2011.

Brandhuber, Philip J. et al., "Methods for the Detection of Residual Concentrations of Hydrogen Peroxide in Advanced Oxidation Processes" WateReuse Foundation, pp. 1-71, 2009 2009.

Ecolab USA Inc., PCT/US2016/061470 filed Nov. 11, 2016, "International Search Report" dated 2016.

Putt, Karson S. et al., "A High-Throughput Microtiter Plate Based Method for the Determination of Peracetic Acid and Hydrogen Peroxide" PLOS ONE, vol. 8, pp. 1-7 Nov. 2013.

Pinkernell, U. et al., "Determination of Peroxyacetic Acid Using High-Performance Liquid Chromatography with External Calibration", Analytical Chemistry, vol. 66, No. 15, pp. 2599-2602, Aug. 1, 1994.

Davies, D. Martin, et al., "Determination of Peracids in the Presence of a Large Excess of Hydrogen Peroxide Using a Rapid and Convenient Spectrophotometric Method", Analyst, vol. 113, pp. 1477-1479, Sep. 1988.

Schick, Roland, et al., "Fluorometric Determination of Low Concentrations of H2O2 in Water: Comparison with Two Other Methods and Application to Environmental Samples and Drinking-Water Treatment", Wat. Res., vol. 31, No. 6, pp. 1371-1378, 1997.

\* cited by examiner

FLUORESCENCE ASSAY FOR QUANTIFICATION OF PICOLINATE AND OTHER COMPOUNDS IN OXIDIZERS AND OXIDIZING COMPOSITIONS

FIELD OF THE INVENTION

This disclosure generally relates to systems and methods for measuring concentration of chemicals in a solution. More particularly, this disclosure relates to systems and methods involving a fluorometer and sample preparation for measuring concentration of chemicals in an oxidizing solution.

BACKGROUND OF THE INVENTION

Cleaning operations in public facilities such as restaurants, hotels, food and beverage plants, hospitals, etc. typically use a cleaning product having sanitizing, disinfecting and/or antimicrobial properties. In some cases, cleaning products may interact with certain chemical compounds (e.g., dipicolinic acid) present in some microbial spores to destroy microbes. Alternatively, certain chemical compounds may be added to cleaning products to improve their chemical stability and/or shelf-life. For instance, dipicolinic acid (DPA) can be added to certain cleaning products to improve their resistance to heat, thereby reducing the rate of degradation of the cleaning products when exposed to heat and extending the use of such cleaning products in Dipicolinic acid exhibits fluorescence when excited by electromagnetic radiation of certain wavelengths, the concentration of dipicolinic acid in a solution can be measured by measuring the fluorescence of the solution. The intensity of fluorescence emitted by the solution may depend on the concentration of dipicolinic acid in the solution. For instance, the intensity of fluorescence emitted by the solution may be directly proportion to the concentration of dipicolinic acid. By measuring the intensity of the fluorescence emitted by dipicolinic acid, the concentration of dipicolinic acid can therefore be determined.

Fluorometers for measuring fluorescence of a sample are relatively well known. An exemplary fluorometer for measuring fluorescence is disclosed in U.S. Pat. No. 8,269,193 and U.S. Pat. No. 8,352,207 both assigned to Ecolab Inc., St. Paul, Minn., the disclosure of each of which is here by incorporated by reference in its entirety. Fluorometers generally have a source of electromagnetic radiation that can excite a sample (e.g., dipicolinic acid solution of an unknown concentration), and a detector adapted to measure the intensity of fluorescence emitted by the electromagnetic radiation.

In many situations the concentration of a substance of interest (e.g., dipicolinic acid) in a solution (e.g., cleaning solution) may be very low. For instance, regulatory requirements may necessitate that only a minimum level of the substance of interest (e.g., dipicolinic acid) is present in a target area (e.g., a healthcare facility, food and beverage production and packaging facility). In such cases, the intensity of fluorescence emitted by such substances of interest can be proportional to their concentration. Low concentrations (e.g., on the order of a few hundred parts per billion) may result in decrease in intensity of emitted fluorescence. For instance, the fluorescence may decrease directly proportional to the decrease in concentration (or by diluting the substance of interest). Typical fluorometers known in the art may not be able to measure such low levels of fluorescence with high accuracy and sensitivity.

SUMMARY OF THE INVENTION

The invention includes methods and compositions useful for fluorescence detection of the concentration of a target analyte when present in an oxidizing composition. Fluorescence detection, while quick and cost effective is limited by the variability of fluorescence, and is dependent on numerous factors, including temperature and pH. Changes to these parameters can bias the final result. Oxidizers can chemically interfere with fluorescence, thus tainting the effectiveness of analysis methods employing the same. The detection of concentration of stabilizing agents or other chemicals in these compositions typically requires the use of labor intensive methods such as high performance liquid chromatography.

According to the invention an effective amount of a reducing agent, such as a sulfate, more specifically a thiosulfate, is added to an assay sample to eliminate interference with the fluorescent absorbance. Other reducing agents useful according to the invention include sulfites, phosphites, hypophosphites, phosphorous acid, oxalic acid, formic acid, ascorbic acid, etc. Thus compositions with strong oxidizers, such as peracetic acid, peroctanoic acid, including performic compositions comprising the same, hydrogen peroxide, and other oxidizers and oxidizing agents can now effectively be analyzed for the concentration of various chemicals, such as DPA. The addition of reducing agents such as sodium thiosulfate to the sample solution neutralizes peracid and peroxide species in the formula, mitigating the effects of the peracid equilibrium on the fluorescence intensity. Pre- and post-equilibration readings of the oxidizing composition may be effectively assayed with thiosulfate addition. The neutralizing agent must be present in slight excess of the peracid to ensure that available peracid is neutralized.

Strong oxidizing compositions frequently include the use of stabilizers such as picolinic acid, (including dipicolinic or tripicolinic) and other various components which must be quantified for quality control and other reasons. See for example, United States Published Application Number 20140097144, filed Apr. 10, 2014, entitled Stable Percarboxylic Acid Compositions And Uses Thereof, the disclosure of which is hereby incorporated by reference.

In another aspect of the invention, picolinic acid, DPA, or tripicolinic acid (TPA) can be measured fluorometrically by the addition of an effective amount of terbium chloride $TbCl_3$ to a sample solution. Terbium chloride complexes with DPA in solution in a 1:3 ratio to form a complex. Here again, the $TbCl_3$ must be present in slight excess to ensure that all available DPA is bound. The $TbCl_3$.DPA complex has an excitation wavelength of 272 nm and an emission wavelength of 545 nm.

Thus the invention includes sample preparation for fluorescence detection by adding a sufficient amount of a reducing agent to a sample of a composition that includes an oxidizing agent, so that peracid is neutralized. In the case of assaying for DPA, the invention also includes the step of adding a sufficient amount of $TbCl_3$ to bind to DPA. After the sample preparation steps the fluorescence may be measured by any technique known to those of skill in the art, such as with the use of a fluorometer.

The details of one or more embodiments of the invention are set forth in the accompanying drawings and the description below. Other features, objects, and advantages will be apparent from the description and drawings, and from the claims.

BRIEF DESCRIPTION OF THE DRAWINGS

The following drawings are illustrative of particular embodiments of the present invention and therefore do not limit the scope of the invention. The drawings are not necessarily to scale (unless so stated) and are intended for use in conjunction with the explanations in the following detailed description. Embodiments of the invention will hereinafter be described in conjunction with the appended drawings, wherein like numerals denote like elements.

DETAILED DESCRIPTION OF THE INVENTION

Figure 1:
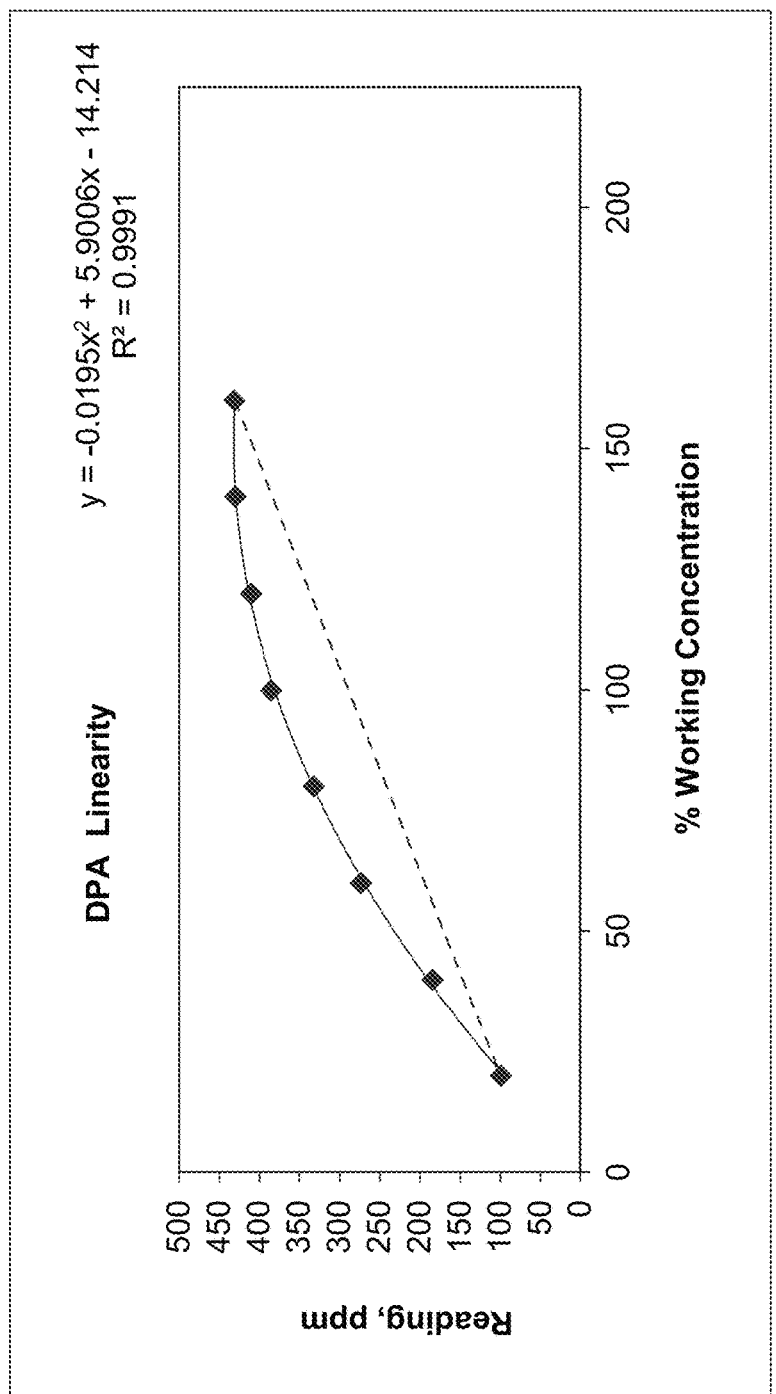
FIG. 1 is a graph showing DPA ppm readings as determined by fluorometry at different concentrations of sample product (peracid) and TbCl3 at a 1:200 dilution. Dotted line shows a perfectly linear relationship.

The following detailed description is exemplary in nature and is not intended to limit the scope, applicability, or configuration of the invention in any way. Rather, the following description provides some practical illustrations for implementing exemplary embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Commercially available peroxycarboxylic acid compositions generally have significantly less, or roughly equal, weight amounts of peroxycarboxylic acid than hydrogen peroxide. It is known that among other factors, the ratio of hydrogen peroxide to peroxycarboxylic acid plays a significant role in the stability of the peroxycarboxylic acid compositions. The higher the ratio of hydrogen peroxide to peroxycarboxylic acid, the more stable of the composition. Some commonly available peroxycarboxylic acid compositions have a ratio of about 1.5 to 1 hydrogen peroxide to peroxycarboxylic acid. While compositions with higher ratio of peroxycarboxylic acid to hydrogen peroxide are commercially available, these compositions are in small packaging sizes limited by self-accelerating decomposition temperature (SADT) transportation limitations and require controlled temperature storage due to the limited stability of the compositions.

These compositions can be difficult to assay by fluorometry due to these changing ratios of peroxycarboxylic acid and hydrogen peroxide. According to one aspect of the invention compositions such as peroxycarboxylic acid compositions or other oxidizing compositions may be assayed by fluorometry with a sample preparation step that includes appropriate dilution and the addition of a reducing agent.

Various chemicals are used in peroxycarboxylic acid compositions to stabilize the compositions. For example, pyridine carboxylic acid based stabilizers, such as picolinic acid and salts, pyridine-2,6-dicarboxylic acid and salts, and phosphonate based stabilizers, such as phosphoric acid and salts, pyrophosphoric acid and salts and most commonly 1-hydroxyethylidene-1,1-diphosphonic acid (HEDP) and salts, are used. When used individually at the right level, these stabilizers can significantly improve the stability of the peroxycarboxylic acid compositions, and for the conventional peroxycarboxylic acid compositions, the stability profile achieved with these stabilizers allows for the commercial use of these compositions. Assaying for the amount of these stabilizing chemicals for quality assurances or other purposes can now be achieved with the use of fluorometry. For example, for picolinic acid, the use of terbium chloride in the sample preparation will allow for fluorescence detection. Fluorometers according to some embodiments of the invention are suitable for detecting the amount of picolinic acid present in compositions. Dipicolinic acid and terbium chloride solution may produce fluorescence intensity linearly proportional to the concentration, thereby enhancing the sensitivity of concentration and/or fluorescent measurement.

A fluorometer can be useful for measuring fluorescence emitted by certain samples. Moreover, the fluorometer can facilitate determining the concentration of certain samples in a solution based on the measured fluorescence. Such embodiments can be useful for measuring intensity of fluorescence emitted by samples such as dipicolinic acid and other chemicals (e.g., found in cleaning products). Based on the measured intensity of emitted fluorescence, the concentration of a target analyte in a solution (e.g., a sanitizer, disinfectant, detergent, and the like) can be determined for oxidizing compositions.

For clarity of disclosure, and not by way of limitation, the detailed description of the invention is divided into the subsections that follow.

Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

The embodiments of this invention are not limited to particular peroxycarboxylic acid compositions and methods for using the same, which can vary and are understood by skilled artisans. It is further to be understood that all terminology used herein is for the purpose of describing particular embodiments only, and is not intended to be limiting in any manner or scope. For example, all units, prefixes, and symbols may be denoted in its SI accepted form. Numeric ranges recited within the specification are inclusive of the numbers defining the range and include each integer within the defined range.

It should be noted that, as used in this specification and the appended claims, the singular forms "a," "an," and "the" include plural referents unless the content clearly dictates otherwise. Thus, for example, reference to a composition containing "a compound" includes a composition having two or more compounds. It should also be noted that the term "or" is generally employed in its sense including "and/or" unless the content clearly dictates otherwise.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

As used herein, the term "about" refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "cleaning," as used herein, means to perform or aid in soil removal, bleaching, microbial population reduction, or combination thereof. For the purpose of this patent application, successful microbial reduction is achieved when the microbial populations are reduced by at least about 50%, or by significantly more than is achieved by a wash with water. Larger reductions in microbial population provide greater levels of protection.

As used herein, "consisting essentially of" means that the methods and compositions may include additional steps, components, ingredients or the like, but only if the additional steps, components and/or ingredients do not materially alter the basic and novel characteristics of the claimed methods and compositions.

As used herein, the term "disinfectant" refers to an agent that kills all vegetative cells including most recognized pathogenic microorganisms, using the procedure described in A.O.A.C. Use Dilution Methods, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

As used herein, the term "free," "no," "substantially no" or "substantially free" refers to a composition, mixture, or ingredient that does not contain a particular compound or to which a particular compound or a particular compound-containing compound has not been added. In some embodiments, the reduction and/or elimination of hydrogen peroxide according to embodiments provide hydrogen peroxide-free or substantially-free compositions. Should the particular compound be present through contamination and/or use in a minimal amount of a composition, mixture, or ingredients, the amount of the compound shall be less than about 3 wt-%. More preferably, the amount of the compound is less than 2 wt-%, less than 1 wt-%, and most preferably the amount of the compound is less than 0.5 wt-%.

As used herein, the term "microorganism" refers to any noncellular or unicellular (including colonial) organism. Microorganisms include all prokaryotes. Microorganisms include bacteria (including cyanobacteria), spores, lichens, fungi, protozoa, virions, viroids, viruses, phages, and some algae. As used herein, the term "microbe" is synonymous with microorganism.

As used herein, the terms "mixed" or "mixture" when used relating to "percarboxylic acid composition," "percarboxylic acids," "peroxycarboxylic acid composition" or "peroxycarboxylic acids" refer to a composition or mixture including more than one percarboxylic acid or peroxycarboxylic acid.

As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in Germicidal and Detergent Sanitizing Action of Disinfectants, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25.+−0.2° C., against several test organisms.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition.

As used herein, the term "water" for treatment according to the invention includes a variety of sources, such as freshwater, pond water, sea water, salt water or brine source, brackish water, recycled water, or the like. Waters are also understood to optionally include both fresh and recycled water sources (e.g. "produced waters"), as well as any combination of waters for treatment according to the invention. As used herein, "weight percent," "wt-%," "percent by weight," "% by weight," and variations thereof refer to the concentration of a substance as the weight of that substance divided by the total weight of the composition and multiplied by 100. It is understood that, as used here, "percent," "%," and the like are intended to be synonymous with "weight percent," "wt-%," etc.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Detection of Target Analytes in Oxidizing Compositions

The invention includes methods and compositions useful for fluorescence detection of the concentration of a target analyte when present in an oxidizing composition. The invention involves pretreatment of the sample to be assayed. An effective amount of a reducing agent, such as a sulfate, more specifically a thiosulfate is added to sample preparation to eliminate interference with the fluorescent absorbance. Other reducing agents useful according to the invention include sulfites, phosphites, hypophosphites, phosphorous acid, oxalic acid, formic acid, ascorbic acid, etc. Thus compositions with strong oxidizers, such as peracetic acid, peroctanoic acid, including performic compositions comprising the same, hydrogen peroxide, and other oxidizers and oxidizing agents can now effectively be analyzed for the concentration of various chemicals, such as DPA. The addition of reducing agents such as sodium thiosulfate to the sample test solution is used to neutralize peracid and peroxide species in the formula, mitigating the effects of the peracid equilibrium on the fluorescence intensity. Pre- and post-equilibration readings of the oxidizing composition may be effectively assayed with the thiosulfate addition. The neutralizing agent must be present in slight excess of the peracid to ensure that all available peracid is neutralized.

According to the invention an effective amount of a reducing agent such as sodium thiosulfate is added to a sample solution. The amount of reducing agent must be in slight excess to the amount of peracid to be neutralized. One can use the following to determine the one theoretical minimum amount of reducing agent to add.

Milliliters of reducing agent=(weight of oxidizing chemical in sample, g)(1000 meq/eq) (molarity of reducing agent solution)(Equivalent weight of oxidizing chemical)

Using equivalent weight will take into account the molecular weight of the oxidizing chemical and the stoichiometry of its reaction with the reducing agent. Applicants determined the thiosulfate addition based on iodometric titration demand of sodium thiosulfate and as a general rule, 100 mL will be acceptable. Keeping a minimum ratio of 2:1 (thiosulfate:peroxide in the original pre EQ formula) and following that charge down with dilution, will always result in an excess of thiosulfate in a sample dilution preparation. In one embodiment the thiosulfate must not be greater than about 5% of the solution or the fluorescence is outside of the linear range.

In one embodiment 200 mL of 0.05 sodium thiosulfate is added to water to form a sample solution. 1 mL of oxidizing composition is added to the sample solution (either prior to addition of the neutralizing composition or after the addition of the neutralizing composition) and then the sample solution is assayed fluorometrically In certain embodiments the solution must be diluted to appropriately detect the emitted fluorescence in a desired linear fashion. This may need to be predetermined to set a baseline dilution for components other that the DPA;TbCl$_3$ complex. Dilution with water, preferably deionized water can be necessary up to about 1:1000 and higher for the DPA:terbium chloride complex.

In the event that picolinic acid is the target analyte, the picolinic acid is generally desired to be present at approximately 0.4-0.6 ppm in concentration. Most samples will need to be diluted prior to testing. According the invention substituted or unsubstituted mono, di or tripicolinic acid present in oxidizing compositions may be assayed fluorometrically. Examples of picolinic acids include a compound having the following Formula:

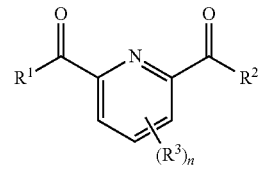

wherein $R^1$ is OH or $-NR^{1a}R^{1b}$, wherein $R^{1a}$ and $R^{1b}$ are independently hydrogen or $(C_1$-$C_6)$ alkyl;
$R^2$ is OH or $-NR^{2a}R^{2b}$, wherein $R^{2a}$ and $R^{2b}$ are independently hydrogen or $(C_1$-$C_6)$ alkyl;
each $R^3$ is independently $(C_1$-$C_6)$alkyl, $(C_2$-$C_6)$alkenyl or $(C_2$-$C_6)$ alkynyl; and
n is a number from zero to 3;
or a salt thereof;
or a compound having the following Formula:

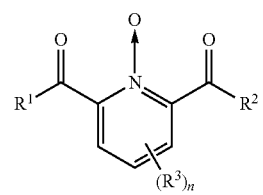

wherein
R¹ is OH or —NR¹ᵃR¹ᵇ, wherein R¹ᵃ and R¹ᵇ are independently hydrogen or (C₁-C₆)alkyl; R² is OH or —NR²ᵃR²ᵇ, wherein R²ᵃ and R²ᵇ are independently hydrogen or (C₁-C₆)alkyl; each R³ is independently (C₁-C₆)alkyl, (C₂-C₆)alkenyl or (C₂-C₆)alkynyl; and n is a number from zero to 3;

or a salt thereof.

When picolinic acid is the analyte, an additional step of adding an effective amount of terbium chloride is performed. Again, the terbium chloride must be in slight excess of the amount of DPA so that all DPA may be complexed. For example 1 mL of 0.011 TbCl₃ may be added to an assay receptacle with 1 mL of sample per above in addition to the reducing agent to form the sample solution. Because the TbCl₃ complexes the DPA in a 1:3 ratio, the amount of TbCl₃ to add should be at a minimum, in excess of about 1/3 the concentration of the DPA in the sample. This step can occur at any time during the sample preparation. Care must also be taken to find a dilution low enough not to "flood" or max out the signal on the fluorometer.

The details of one or more embodiments of the invention are set forth in the accompanying drawings and the description below. Other features, objects, and advantages will be apparent from the description and drawings, and from the claims.

In an aspect, the reducing agent comprises one or a mixture of reducing agents such as sulfites, bisulfites, borites, metabisulfites (pyrosulfites), sulfoxylates, thiosulfates, dithionites (hydrosulfites), polythionates, and formamidinesulfinic acid and/or salts thereof. The reducing agent or mixture thereof can comprise one or any combination of the foregoing reducing agents. In a preferred embodiment the reducing agent is a thiosulfate, such as sodium thiosulfate.

Terbium chloride complexes with DPA in solution in a 1:3 ratio to form a complex as depicted below:

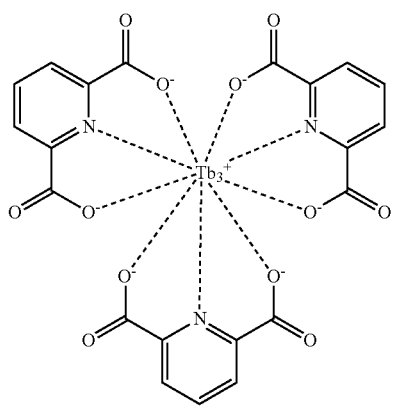

Here again, the TbCl₃ must be present in slight excess to ensure that all available DPA is bound. The TbCl₃.DPA complex has an excitation wavelength of 272 nm and an emission wavelength of 545 nm.

Oxidizing Compositions
Percarboxylic Acid Compositions

The present invention relates to assay methods for fluorescence detection of components present in stable and equilibrating percarboxylic acid compositions or other oxidizing compositions. In one aspect, the present invention is directed to assaying a composition, which composition comprises: a C₁-C₂₂ carboxylic acid; hydrogen peroxide; a stabilizing agent, which is a picolinic acid or a compound having the following Formula (IA):

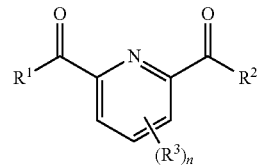

wherein R¹ is OH or —NR¹ᵃR¹ᵇ, wherein R¹ᵃ and R¹ᵇ are independently hydrogen or (C₁-C₆)alkyl;

R² is OH or —NR²ᵃR²ᵇ, wherein R²ᵃ and R²ᵇ are independently hydrogen or (C₁-C₆)alkyl;

each R³ is independently (C₁-C₆)alkyl, (C₂-C₆)alkenyl or (C₂-C₆)alkynyl; and n is a number from zero to 3;

or a salt thereof;

or a compound having the following Formula:

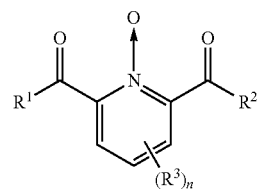

wherein
R¹ is OH or —NR¹ᵃR¹ᵇ, wherein R¹ᵃ and R¹ᵇ are independently hydrogen or (C₁-C₆)alkyl; R² is OH or —NR²ᵃR²ᵇ, wherein R²ᵃ and R²ᵇ are independently hydrogen or (C₁-C₆)alkyl; each R³ is independently (C₁-C₆)alkyl, (C₂-C₆)alkenyl or (C₂-C₆)alkynyl; and n is a number from zero to 3;

or a salt thereof;

and wherein said hydrogen peroxide has a concentration of at least about 0.1 wt-%, the C₁-C₂₂ percarboxylic acid has a concentration of at least about 2 times of the concentration of said hydrogen peroxide, and said composition has a pH at about 4 or less.

In some embodiments, the present composition is an equilibrated composition that comprises peracid, hydrogen peroxide, carboxylic acid and a solvent, e.g., water. In some embodiments, the present composition does not comprise a mineral acid, e.g., the mineral acids disclosed in WO 91/07375.

The C₁-C₂₂ percarboxylic acid can be used at any suitable concentration relative to the concentration of the hydrogen peroxide. In some embodiments, the C₁-C₂₂ percarboxylic acid has a concentration of at least about 6 times of the concentration of the hydrogen peroxide. In other embodiments, the C₁-C₂₂ percarboxylic acid has a concentration of at least about 10 times of the concentration of the hydrogen peroxide. In still other embodiments, the C₁-C₂₂ percarboxylic acid has a concentration of at least about 6, 7, 8, 9 or 10 times of the concentration of the hydrogen peroxide.

Carboxylic Acid

The present invention includes a carboxylic acid with the peracid composition and hydrogen peroxide. A carboxylic acid includes any compound of the formula R—(COOH)ₙ in which R can be hydrogen, alkyl, alkenyl, alkyne, acylic, alicyclic group, aryl, heteroaryl, or heterocylic group, and n is 1, 2, or 3. Preferably R includes hydrogen, alkyl, or alkenyl. The terms "alkyl," "alkenyl," "alkyne," "acylic," "alicyclic group," "aryl," "heteroaryl," and "heterocyclic group" are as defined below with respect to peracids.

Examples of suitable carboxylic acids according to the equilibrium systems of peracids according to the invention include a variety monocarboxylic acids, dicarboxylic acids, and tricarboxylic acids. Monocarboxylic acids include, for example, formic acid, acetic acid, propanoic acid, butanoic acid, pentanoic acid, hexanoic acid, heptanoic acid, octanoic acid, nonanoic acid, decanoic acid, undecanoic acid, dodecanoic acid, glycolic acid, lactic acid, salicylic acid, acetylsalicylic acid, mandelic acid, etc. Dicarboxylic acids include, for example, adipic acid, fumaric acid, glutaric acid, maleic acid, succinic acid, malic acid, tartaric acid, etc. Tricarboxylic acids include, for example, citric acid, trimellitic acid, isocitric acid, agaicic acid, etc.

In an aspect of the invention, a particularly well suited carboxylic acid is water soluble such as formic acid, acetic acid, propionic acid, butanoic acid, lactic acid, glycolic acid, citric acid, mandelic acid, glutaric acid, maleic acid, malic acid, adipic acid, succinic acid, tartaric acid, etc. Preferably a composition of the invention includes acetic acid, octanoic acid, or propionic acid, lactic acid, heptanoic acid, octanoic acid, or nonanoic acid.

Additional examples of suitable carboxylic acids are employed in sulfoperoxycarboxylic acid or sulfonated peracid systems, which are disclosed in U.S. Patent Publication Nos. 2010/0021557, 2010/0048730 and 2012/0052134 herein incorporated by reference in their entireties.

Any suitable $C_1$-$C_{22}$ carboxylic acid can be used in the present compositions. In some embodiments, the C1-C22 carboxylic acid is a C2-C20 carboxylic acid. In other embodiments, the C1-C22 carboxylic acid is a C1, C2, C3, C4, C5, C6, C7, C8, C9, C10, C11, C12, C13, C14, C15, C16, C17, C18, C19, C20, C21, or C22 carboxylic acid. In still other embodiments, the C1-C22 carboxylic acid comprises acetic acid, octanoic acid and/or sulfonated oleic acid. The C1-C22 carboxylic acid can be used at any suitable concentration. In some embodiments, the C1-C22 carboxylic acid has a concentration from about 10 wt-% to about 90 wt-%. In other embodiments, the C1-C22 carboxylic acid has a concentration from about 20 wt-% to about 80 wt-%. In still other embodiments, the C1-C22 carboxylic acid has a concentration at about 10 wt-%, 20 wt-%, 30 wt-%, 40 wt-%, 50 wt-%, 60 wt-%, 70 wt-%, 80 wt-%, or 90 wt-%.

Peracids

In some aspects, a peracid is included for antimicrobial efficacy in the compositions. As used herein, the term "peracid" may also be referred to as a "percarboxylic acid" or "peroxyacid." Sulfoperoxycarboxylic acids, sulfonated peracids and sulfonated peroxycarboxylic acids are also included within the term "peracid" as used herein. The terms "sulfoperoxycarboxylic acid," "sulfonated peracid," or "sulfonated peroxycarboxylic acid" refers to the peroxycarboxylic acid form of a sulfonated carboxylic acid as disclosed in U.S. Patent Publication Nos. 2010/0021557, 2010/0048730 and 2012/0052134 which are incorporated herein by reference in their entireties. A peracid refers to an acid having the hydrogen of the hydroxyl group in carboxylic acid replaced by a hydroxy group. Oxidizing peracids may also be referred to herein as peroxycarboxylic acids.

A peracid includes any compound of the formula R—(COOOH)$_n$ in which R can be hydrogen, alkyl, alkenyl, alkyne, acylic, alicyclic group, aryl, heteroaryl, or heterocyclic group, and n is 1, 2, or 3, and named by prefixing the parent acid with peroxy. Preferably R includes hydrogen, alkyl, or alkenyl. The terms "alkyl," "alkenyl," "alkyne," "acylic," "alicyclic group," "aryl," "heteroaryl," and "heterocyclic group" are as defined herein.

As used herein, the term "alkyl" includes a straight or branched saturated aliphatic hydrocarbon chain having from 1 to 22 carbon atoms, such as, for example, methyl, ethyl, propyl, isopropyl (1-methylethyl), butyl, tert-butyl (1,1-dimethylethyl), and the like. The term "alkyl" or "alkyl groups" also refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

The term "alkenyl" includes an unsaturated aliphatic hydrocarbon chain having from 2 to 12 carbon atoms, such as, for example, ethenyl, 1-propenyl, 2-propenyl, 1-butenyl, 2-methyl-1-propenyl, and the like. The alkyl or alkenyl can be terminally substituted with a heteroatom, such as, for example, a nitrogen, sulfur, or oxygen atom, forming an aminoalkyl, oxyalkyl, or thioalkyl, for example, aminomethyl, thioethyl, oxypropyl, and the like. Similarly, the above alkyl or alkenyl can be interrupted in the chain by a heteroatom forming an alkylaminoalkyl, alkylthioalkyl, or alkoxyalkyl, for example, methylaminoethyl, ethylthiopropyl, methoxymethyl, and the like.

Further, as used herein the term "alicyclic" includes any cyclic hydrocarbyl containing from 3 to 8 carbon atoms. Examples of suitable alicyclic groups include cyclopropanyl, cyclobutanyl, cyclopentanyl, etc. The term "heterocyclic" includes any closed ring structures analogous to carbocyclic groups in which one or more of the carbon atoms in the ring is an element other than carbon (heteroatom), for example, a nitrogen, sulfur, or oxygen atom. Heterocyclic groups may be saturated or unsaturated. Examples of suitable heterocyclic groups include for example, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan. Additional examples of suitable heterocyclic groups include groups derived from tetrahydrofurans, furans, thiophenes, pyrrolidines, piperidines, pyridines, pyrrols, picoline, coumaline, etc.

In some embodiments, alkyl, alkenyl, alicyclic groups, and heterocyclic groups can be unsubstituted or substituted by, for example, aryl, heteroaryl, $C_{1-4}$ alkyl $C_{1-4}$ alkenyl, C $C_{1-4}$ alkoxy, amino, carboxy, halo, nitro, cyano, —$SO_3H$, phosphono, or hydroxy. When alkyl, alkenyl, alicyclic group, or heterocyclic group is substituted, preferably the substitution is $C_{1-4}$ alkyl, halo, nitro, amido, hydroxy, carboxy, sulpho, or phosphono. In one embodiment, R includes alkyl substituted with hydroxy. The term "aryl" includes aromatic hydrocarbyl, including fused aromatic rings, such as, for example, phenyl and naphthyl. The term "heteroaryl" includes heterocyclic aromatic derivatives having at least one heteroatom such as, for example, nitrogen, oxygen, phosphorus, or sulfur, and includes, for example, furyl, pyrrolyl, thienyl, oxazolyl, pyridyl, imidazolyl, thiazolyl, isoxazolyl, pyrazolyl, isothiazolyl, etc. The term "heteroaryl" also includes fused rings in which at least one ring is aromatic, such as, for example, indolyl, purinyl, benzofuryl, etc.

In some embodiments, aryl and heteroaryl groups can be unsubstituted or substituted on the ring by, for example, aryl, heteroaryl, alkyl, alkenyl, alkoxy, amino, carboxy, halo, nitro, cyano, —$SO_3H$, phosphono, or hydroxy. When aryl, aralkyl, or heteroaryl is substituted, preferably the substitution is $C_{1-4}$ alkyl, halo, nitro, amido, hydroxy, carboxy, sulpho, or phosphono. In one embodiment, R includes aryl substituted with $C_{1-4}$ alkyl.

Peracids suitable for use include any peroxycarboxylic acids, including varying lengths of peroxycarboxylic and percarboxylic acids (e.g. C1-22) that can be prepared from the acid-catalyzed equilibrium reaction between a carboxylic acid described above and hydrogen peroxide. A peroxycarboxylic acid can also be prepared by the auto-oxidation of aldehydes or by the reaction of hydrogen peroxide with an acid chloride, acid hydride, carboxylic acid anhydride, or sodium alcoholate. Alternatively, peracids can be prepared through non-equilibrium reactions, which may be generated for use in situ, such as the methods disclosed in U.S. patent application Ser. Nos. 13/331,304 and 13/331,486 each titled "In Situ Generation of Peroxycarboxylic Acids at Alkaline pH, and Methods of Use Thereof," which are incorporated herein by reference. Preferably a composition of the invention includes peroxyacetic acid, peroxyoctanoic acid, peroxypropionic acid, peroxylactic acid, peroxyheptanoic acid, peroxyoctanoic acid and/or peroxynonanoic acid.

In some embodiments, a peroxycarboxylic acid includes at least one water-soluble peroxycarboxylic acid in which R includes alkyl of 1-22 carbon atoms. For example, in one embodiment, a peroxycarboxylic acid includes peroxyacetic acid. In another embodiment, a peroxycarboxylic acid has R that is an alkyl of 1-22 carbon atoms substituted with hydroxy. Methods of preparing peroxyacetic acid are known to those of skill in the art including those disclosed in U.S. Pat. No. 2,833,813, which is herein incorporated herein by reference. In another embodiment, a sulfoperoxycarboxylic acid has the following formula:

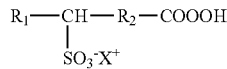

wherein $R_1$ is hydrogen, or a substituted or unsubstituted alkyl group; $R_2$ is a substituted or unsubstituted alkylene group; X is hydrogen, a cationic group, or an ester forming moiety; or salts or esters thereof. In additional embodiments, a sulfoperoxycarboxylic acid is combined with a single or mixed peroxycarboxylic acid composition, such as a sulfoperoxycarboxylic acid (PSOA) with peroxyacetic acid (POOA) and peroxyoctanoic acid (POAA).

In other embodiments, a mixed peracid is employed, such as a peroxycarboxylic acid including at least one peroxycarboxylic acid of limited water solubility in which R includes alkyl of 5-22 carbon atoms and at least one water-soluble peroxycarboxylic acid in which R includes alkyl of 1-4 carbon atoms. For example, in one embodiment, a peroxycarboxylic acid includes peroxyacetic acid and at least one other peroxycarboxylic acid such as those named above. Preferably a composition of the invention includes peroxyacetic acid and peroxyoctanoic acid. Other combinations of mixed peracids are well suited for use in the current invention.

In another embodiment, a mixture of peracetic acid and peroctanoic acid is used to treat a water source, such as disclosed in U.S. Pat. No. 5,314,687 which is herein incorporated by reference in its entirety. In an aspect, the peracid mixture is a hydrophilic peracetic acid and a hydrophobic peroctanoic acid, providing antimicrobial synergy. In an aspect, the synergy of a mixed peracid system allows the use of lower dosages of the peracids.

In another embodiment, a tertiary peracid mixture composition, such as peroxysulfonated oleic acid, peracetic acid and peroctanoic acid are used to treat a water source, such as disclosed in U.S. Patent Publication No. 2010/00021557 which is incorporated herein by reference in its entirety. A combination of the three peracids provides significant antimicrobial synergy providing an efficient antimicrobial composition for the water treatment methods according to the invention. In addition, it is thought the high acidity built in the composition assists in removing chemical contaminants from the water (e.g. sulfite and sulfide species).

Advantageously, a combination of peroxycarboxylic acids provides a composition with desirable antimicrobial activity in the presence of high organic soil loads. The mixed peroxycarboxylic acid compositions often provide synergistic micro efficacy. Accordingly, compositions of the invention can include a peroxycarboxylic acid, or mixtures thereof.

Various commercial formulations of peracids are available, including for example, peracetic acid (15%) available as EnviroSan (EcolabInc., St. Paul Minn.). Most commercial peracid solutions state a specific percarboxylic acid concentration without reference to the other chemical components in a use solution. However, it should be understood that commercial products, such as peracetic acid, will also contain the corresponding carboxylic acid (e.g. acetic acid), hydrogen peroxide and water.

Any suitable $C_1$-$C_{22}$ carboxylic acid can be used in the present compositions. In some embodiments, the $C_1$-$C_{22}$ carboxylic acid is a $C_2$-$C_{20}$ carboxylic acid. In other embodiments, the $C_1$-$C_{22}$ carboxylic acid is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ carboxylic acid. In still other embodiments, the $C_1$-$C_{22}$ carboxylic acid comprises acetic acid, octanoic acid and/or sulfonated oleic acid.

The $C_1$-$C_{22}$ percarboxylic acid can be used at any suitable concentration. In some embodiments, the $C_1$-$C_{22}$ percarboxylic acid has a concentration from about 1 wt-% to about 40 wt-%. In other embodiments, the $C_1$-$C_{22}$ percarboxylic acid has a concentration from about 1 wt-% to about 20 wt-%. In still other embodiments, the $C_1$-$C_{22}$ percarboxylic acid has a concentration at about 1 wt-%, 2 wt-%, 3 wt-%, 4 wt-%, 5 wt-%, 6 wt-%, 7 wt-%, 8 wt-%, 9 wt-%, 10 wt-%, 11 wt-%, 12 wt-%, 13 wt-%, 14 wt-%, 15 wt-%, 16 wt-%, 17 wt-%, 18 wt-%, 19 wt-%, 20 wt-%, 25 wt-%, 30 wt-%, 35 wt-%, or 40 wt-%.

Hydrogen Peroxide

The present invention includes assaying compositions which include hydrogen peroxide. Hydrogen peroxide, $H_2O_2$, provides the advantages of having a high ratio of active oxygen because of its low molecular weight (34.014 g/mole) and being compatible with numerous substances that can be treated by methods of the invention because it is a weakly acidic, clear, and colorless liquid. Another advantage of hydrogen peroxide is that it decomposes into water and oxygen. It is advantageous to have these decomposition products because they are generally compatible with substances being treated. For example, the decomposition products are generally compatible with metallic substance (e.g., substantially noncorrosive) and are generally innocuous to incidental contact and are environmentally friendly.

In one aspect of the invention, hydrogen peroxide is initially in an antimicrobial peracid composition in an amount effective for maintaining equilibrium between a carboxylic acid, hydrogen peroxide, a solvent such as water, and a peracid. The amount of hydrogen peroxide should not exceed an amount that would adversely affect the antimicrobial activity of a composition of the invention. In further aspects of the invention, hydrogen peroxide concentration is significantly reduced within an antimicrobial peracid composition, preferably containing hydrogen peroxide at a concentration as close to zero as possible. That is, the concentration of hydrogen peroxide is minimized, through the use of a selected catalase or peroxidase enzymes according to the invention. In further aspects, the concentration of hydrogen peroxide is reduced and/or eliminated as a result of distilled equilibrium peracid compositions, other catalysts for hydrogen peroxide decomposition (e.g. biomimetic complexes) and/or the use of anionic perhydrolysis of esters (e.g. triacetin) to obtain peracids with very low hydrogen peroxide.

In some embodiments, an advantage of minimizing the concentration of hydrogen peroxide is that antimicrobial activity of a composition of the invention is improved as compared to conventional equilibrium peracid compositions. Without being limited to a particular theory of the invention, significant improvements in antimicrobial efficacy result from enhanced peracid stability from the reduced hydrogen peroxide concentration in use solution.

The hydrogen peroxide can be used at any suitable concentration. In some embodiments, the hydrogen peroxide has a concentration from about 0.5 wt-% to about 10 wt-%. In other embodiments, the hydrogen peroxide has a concentration from about 1 wt-% to about 2 wt-%. In still other embodiments, the hydrogen peroxide has a concentration at about 0.5 wt-%, 1 wt-%, 2 wt-%, 3 wt-%, 4 wt-%, 5 wt-%, 6 wt-%, 7 wt-%, 8 wt-%, 9 wt-%, or 10 wt-%. In yet other embodiments, the hydrogen peroxide has a concentration at about 1 wt-%, 1.1 wt-%, 1.2 wt-%, 1.3 wt-%, 1.4 wt-%, 1.5 wt-%, 1.6 wt-%, 1.7 wt-%, 1.8 wt-%, 1.9 wt-%, or 2 wt-%. In some embodiments, the $C_1$-$C_{22}$ carboxylic acid is acetic acid and the $C_1$-$C_{22}$ percarboxylic acid is peracetic acid. In other embodiments, the $C_1$-$C_{22}$ carboxylic acid, e.g., acetic acid, has a concentration of about 70 wt-%, the $C_1$-$C_{22}$ percarboxylic acid, e.g., peracetic acid, has a concentration of about 15 wt-%, and the hydrogen peroxide has a concentration of at least about 1 wt-%.

Any of the above components either together or individually may be present in an oxidizing composition useful in the present methods of assay. These compositions have any of a number of uses such as bleaches, antimicrobial compositions, cleaning composition and the like. These compositions typically also include any of a number of additional components, the presence and concentration of which may be ascertained according to the invention. Some examples of such additional components are listed below.

Stabilizing Agents

In some aspects, more than one type of stabilizer is used in the composition in addition to DPA. In some embodiments, at least one stabilizer is a phosphonic acid or a derivative thereof. Without wishing to be bound by any particular theory, it is thought that in addition to functioning as a stabilizer through the chelating of transition metal ions, phosphonic acid based stabilizers such as HEDP, also act as an acid catalyst and aid in the formation of the peroxycarboxylic acid from the corresponding carboxylic acid and hydrogen peroxide. In some embodiments, a pyridine carboxylic acid based stabilizer is used as a second stabilizer. Pyridine carboxylic acids such as 2,6-pyridinedicarboxylic acid (DPA), are well known chelators for metal ions. It is thought that by using two different types of stabilizers, the transition metals responsible for the catalytic decomposition of peroxycarboxylic acids are more efficiently deactivated by forming a more stable complex(es) involving both chelators.

Any suitable stabilizing agent can be used in the present compositions. In some embodiments, the stabilizing agent is a picolinic acid, or a salt thereof. In other embodiments, the stabilizing agent is 2,6-pyridinedicarboxylic acid, or a salt thereof. The stabilizing agent can be used at any suitable concentration. In some embodiments, the stabilizing agent has a concentration from about 0.005 wt-% to about 5 wt-%. In other embodiments, the stabilizing agent has a concentration from about 0.05 wt-% to about 0.15 wt-%. In still other embodiments, the stabilizing agent has a concentration at about 0.005 wt-%, 0.01 wt-%, 0.1 wt-%, 1 wt-%, 2 wt-%, 3 wt-%, 4 wt-%, or 5 wt-%. In yet other embodiments, the stabilizing agent has a concentration at about 0.05 wt-%, 0.06 wt-%, 0.07 wt-%, 0.08 wt-%, 0.09 wt-%, 0.10 wt-%, 0.11 wt-%, 0.12 wt-%, 0.13 wt-%, 0.14 wt-%, or 0.15 wt-%. Any suitable second stabilizing agent can be used in the present compositions. In some embodiments, the second stabilizing agent is 1-hydroxy ethylidene-1,1-diphosphonic acid (HEDP), or a salt thereof. The second stabilizing agent can be used at any suitable concentration. In some embodiments, the second stabilizing agent has a concentration from about 0.1 wt-% to about 10 wt-%, e.g., 0.1 wt-%, 0.5 wt-%, 1 wt-%, 2 wt-%, 3 wt-%, 4 wt-%, 5 wt-%, 6 wt-%, 7 wt-%, 8 wt-%, 9 wt-%, or 10 wt-%. In other embodiments, the second stabilizing agent has a concentration from about 0.5 wt-% to about 5 wt-%, e.g., 0.5 wt-%, 1 wt-%, 1.5 wt-%, 2 wt-%, 2.5 wt-%, 3 wt-%, 3.5 wt-%, 4 wt-%, 4.5 wt-% or 5 wt-%. In still other embodiments, the second stabilizing agent has a concentration from about 0.6 wt-% to about 1.8 wt-%, e.g., 0.6 wt-%, 0.7 wt-%, 0.8 wt-%, 0.9 wt-%, 1.0 wt-%, 1.1 wt-%, 1.2 wt-%, 1.3 wt-%, 1.4 wt-%, 1.5 wt-%, 1.6 wt-%, 1.7 wt-%, 1.8 wt-%.

In some embodiments, the present composition can further comprise a substance that aids solubilization of the stabilizing agent(s). Exemplary substances that can aid solubilization of the stabilizing agent(s) include hydrotropes such as sodium xylene sulfonate, sodium cumene sulfonates, and surfactants, such as anionic surfactants and nonionic surfactants.

The present compositions can retain any suitable level or percentage of the $C_1$-$C_{22}$ percarboxylic acid activity under the usual packaging, storage, transportation and/or use condition(s). In some embodiments, the present compositions retain at least about 80% of the $C_1$-$C_{22}$ percarboxylic acid activity after storage of about 30 days at about 50° C. Preferably, the present compositions retain at least about 85%, 90% or higher percentage of the $C_1$-$C_{22}$ percarboxylic acid activity after storage of about 30 days at about 50° C.

Surfactants

In some embodiments, the oxidizing compositions include a surfactant. Surfactants suitable for use with oxidizing compositions include, but are not limited to, nonionic surfactants, anionic surfactants, and zwitterionic surfactants. In some embodiments, the compositions of the include about 10 wt % to about 50 wt % of a surfactant. In other embodiments the compositions include about 15 wt % to about 30% of a surfactant. In still yet other embodiments, the compositions include about 25 wt % of a surfactant. In some embodiments, the compositions include about 100 ppm to about 1000 ppm of a surfactant.

Nonionic Surfactants

Suitable nonionic surfactants suitable for use with the compositions of the present invention include alkoxylated surfactants. Suitable alkoxylated surfactants include EO/PO copolymers, capped EO/PO copolymers, alcohol alkoxylates, capped alcohol alkoxylates, mixtures thereof, or the like. Suitable alkoxylated surfactants for use as solvents include EO/PO block copolymers, such as the Pluronic and reverse Pluronic surfactants; alcohol alkoxylates, such as Dehypon LS-54 (R-(EO)$_5$(PO)$_4$) and Dehypon LS-36 (R-(EO)$_3$(PO)$_6$); and capped alcohol alkoxylates, such as Plurafac LF221 and Tegoten EC11; mixtures thereof, or the like.

Semi-Polar Nonionic Surfactants

The semi-polar type of nonionic surface active agents are another class of nonionic surfactant useful in compositions of the present invention. Semi-polar nonionic surfactants include the amine oxides, phosphine oxides, sulfoxides and their alkoxylated derivatives.

Amine oxides are tertiary amine oxides corresponding to the general formula:

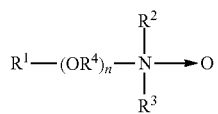

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkylene or a hydroxyalkylene group containing 2 to 3 carbon atoms; and n ranges from 0 to about 20. An amine oxide can be generated from the corresponding amine and an oxidizing agent, such as hydrogen peroxide.

Useful water soluble amine oxide surfactants are selected from the octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, isododecyldimethyl amine oxide, tridecyldimethylamine oxide, tetradecyldimethylamine oxide, pentadecyldimethylamine oxide, hexadecyldimethylamine oxide, heptadecyldimethyl- amine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl) amine oxide, 3,6,9-trioctadecyldimethylamine oxide and 3-dodecoxy-2-hydroxypropyldi-(2-hydroxyethyl)amine oxide.

Anionic Surfactants

Anionic sulfate surfactants suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl) glucamine sulfates, and sulfates of alkylpolysaccharides such as the sulfates of alkylpolyglucoside, and the like. Also included are the alkyl sulfates, alkyl poly(ethyleneoxy) ether sulfates and aromatic poly(ethyleneoxy) sulfates such as the sulfates or condensation products of ethylene oxide and nonyl phenol (usually having 1 to 6 oxyethylene groups per molecule).

Anionic sulfonate surfactants suitable for use in the present compositions also include alkyl sulfonates, the linear and branched primary and secondary alkyl sulfonates, and the aromatic sulfonates with or without substituents.

Anionic carboxylate surfactants suitable for use in the present compositions include carboxylic acids (and salts), such as alkanoic acids (and alkanoates), ester carboxylic acids (e.g. alkyl succinates), ether carboxylic acids, and the like. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylgluamates, acyl peptides, sarcosinates (e.g. N-acyl sarcosinates), taurates (e.g. N-acyl taurates and fatty acid amides of methyl tauride), and the like.

Suitable anionic surfactants include alkyl or alkylaryl ethoxy carboxylates of the following formula:

$$R—O—(CH_2CH_2O)_n(CH_2)_m—CO_2X \qquad (3)$$

in which R is a $C_8$ to $C_{22}$ alkyl group or

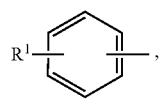

in which $R^1$ is a $C_4$-$C_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In some embodiments, n is an integer of 4 to 10 and m is 1. In some embodiments, R is a $C_8$-$C_{16}$ alkyl group. In some embodiments, R is a $C_{12}$-$C_{14}$ alkyl group, n is 4, and m is 1.

In other embodiments, R is

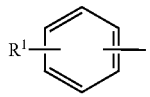

and $R^1$ is a $C_6$-$C_{12}$ alkyl group. In still yet other embodiments, $R^1$ is a $C_9$ alkyl group, n is 10 and m is 1.

Such alkyl and alkylaryl ethoxy carboxylates are commercially available. These ethoxy carboxylates are typically available as the acid forms, which can be readily converted to the anionic or salt form. Commercially available carboxylates include, Neodox 23-4, a $C_{12-13}$ alkyl polyethoxy (4) carboxylic acid (Shell Chemical), and Emcol CNP-110, a $C_9$ alkylaryl polyethoxy (10) carboxylic acid (Witco Chemical). Carboxylates are also available from Clariant, e.g. the product Sandopan® DTC, a $C_{13}$ alkyl polyethoxy (7) carboxylic acid.

Amphoteric Surfactants

Amphoteric, or ampholytic, surfactants contain both a basic and an acidic hydrophilic group and an organic hydrophobic group. These ionic entities may be any of anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge.

Amphoteric surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphato, or phosphono. Amphoteric surfactants are subdivided into two major classes known to those of skill in the art and described in "Surfactant Encyclopedia" *Cosmetics & Toiletries*, Vol. 104 (2) 69-71 (1989). The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Amphoteric surfactants can be synthesized by methods known to those of skill in the art. For example, 2-alkyl hydroxyethyl imidazoline is synthesized by condensation and ring closure of a long chain carboxylic acid (or a derivative) with dialkyl ethylenediamine. Commercial amphoteric surfactants are derivatized by subsequent hydrolysis and ring-opening of the imidazoline ring by alkylation—for example with chloroacetic acid or ethyl acetate. During alkylation, one or two carboxy-alkyl groups react to form a tertiary amine and an ether linkage with differing alkylating agents yielding different tertiary amines.

Long chain imidazole derivatives having application in the present invention generally have the general formula:

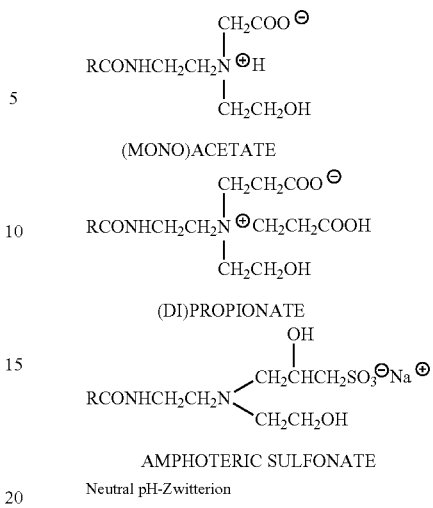

wherein R is an acyclic hydrophobic group containing from about 8 to 18 carbon atoms and M is a cation to neutralize the charge of the anion, generally sodium. Commercially prominent imidazoline-derived amphoterics that can be employed in the present compositions include for example: Cocoamphopropionate, Cocoamphocarboxy-propionate, Cocoamphoglycinate, Cocoamphocarboxy-glycinate, Cocoamphopropyl-sulfonate, and Cocoamphocarboxy-propionic acid. Amphocarboxylic acids can be produced from fatty imidazolines in which the dicarboxylic acid functionality of the amphodicarboxylic acid is diacetic acid and/or dipropionic acid.

The carboxymethylated compounds (glycinates) described herein above frequently are called betaines. Betaines are a special class of amphoteric discussed herein below in the section entitled, Zwitterion Surfactants.

Long chain N-alkylamino acids are readily prepared by reaction $RNH_2$, in which $R=C_8$-$C_{18}$ straight or branched chain alkyl, fatty amines with halogenated carboxylic acids. Alkylation of the primary amino groups of an amino acid leads to secondary and tertiary amines. Alkyl substituents may have additional amino groups that provide more than one reactive nitrogen center. Most commercial N-alkylamine acids are alkyl derivatives of beta-alanine or beta-N(2-carboxyethyl) alanine. Examples of commercial N-alkylamino acid ampholytes having application in this invention include alkyl beta-amino dipropionates, $RN(C_2H_4COOM)_2$ and $RNHC_2H_4COOM$. In an embodiment, R can be an acyclic hydrophobic group containing from about 8 to about 18 carbon atoms, and M is a cation to neutralize the charge of the anion.

Suitable amphoteric surfactants include those derived from coconut products such as coconut oil or coconut fatty acid. Additional suitable coconut derived surfactants include as part of their structure an ethylenediamine moiety, an alkanolamide moiety, an amino acid moiety, e.g., glycine, or a combination thereof; and an aliphatic substituent of from about 8 to 18 (e.g., 12) carbon atoms. Such a surfactant can also be considered an alkyl amphodicarboxylic acid. These amphoteric surfactants can include chemical structures represented as: $C_{12}$-alkyl-C(O)—NH—$CH_2$—$CH_2$—$N^+$($CH_2$—$CH_2$—$CO_2Na)_2$—$CH_2$—$CH_2$—OH or $C_{12}$-alkyl-C(O)—N(H)—$CH_2$—$CH_2$—$N^+$($CH_2$—$CO_2Na)_2$—$CH_2$—$CH_2$—OH. Disodium cocoampho dipropionate is one suitable amphoteric surfactant and is commercially available under the tradename MIRANOL™ FBS from Rhodia Inc., Cranbury, N.J. Another suitable coconut derived amphoteric surfactant with the chemical name disodium cocoampho diacetate is sold under the tradename MIRATAINE™ JCHA, also from Rhodia Inc., Cranbury, N.J.

A typical listing of amphoteric classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Zwitterionic Surfactants

Zwitterionic surfactants can be thought of as a subset of the amphoteric surfactants and can include an anionic charge. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionics generally contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate. Betaine and sultaine surfactants are exemplary zwitterionic surfactants for use herein.

A general formula for these compounds is:

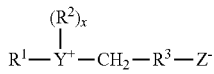

wherein $R^1$ contains an alkyl, alkenyl, or hydroxyalkyl radical of from 8 to 18 carbon atoms having from 0 to 10 ethylene oxide moieties and from 0 to 1 glyceryl moiety; Y is selected from the group consisting of nitrogen, phosphorus, and sulfur atoms; $R^2$ is an alkyl or monohydroxy alkyl group containing 1 to 3 carbon atoms; x is 1 when Y is a sulfur atom and 2 when Y is a nitrogen or phosphorus atom, $R^3$ is an alkylene or hydroxy alkylene or hydroxy alkylene of from 1 to 4 carbon atoms and Z is a radical selected from the group consisting of carboxylate, sulfonate, sulfate, phosphonate, and phosphate groups.

Examples of zwitterionic surfactants having the structures listed above include: 4-[N,N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P-diethyl-P-3,6,9-trioxatetracosanephosphonio]-2-hydroxypropane-1-phosphate; 3-[N,N-dipropyl-N-3-dodecoxy-2-hydroxypropyl-ammonio]-propane-1-phosphonate; 3-(N,N-dimethyl-N-hexadecylammonio)-propane-1-sulfonate; 3-(N,N-dimethyl-N-hexadecylammonio)-2-hydroxy-propane-1-sulfonate; 4-[N,N-di(2(2-hydroxyethyl)-N(2-hydroxydodecyl)ammonio]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; and S[N,N-di(3-hydroxypropyl)-N-hexadecylammonio]-2-hydroxy-pentane-1-sulfate. The alkyl groups contained in said detergent surfactants can be straight or branched and saturated or unsaturated.

The zwitterionic surfactant suitable for use in the present compositions includes a betaine of the general structure:

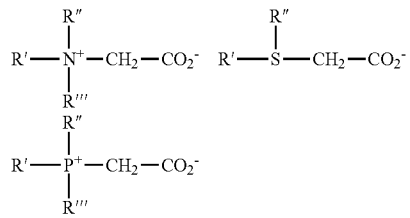

These surfactant betaines typically do not exhibit strong cationic or anionic characters at pH extremes nor do they show reduced water solubility in their isoelectric range. Unlike "external" quaternary ammonium salts, betaines are compatible with anionics. Examples of suitable betaines include coconut acylamidopropyldimethyl betaine; hexadecyl dimethyl betaine; $C_{12\text{-}14}$ acylamidopropylbetaine; $C_{8\text{-}14}$ acylamidohexyldiethyl betaine; 4-$C_{14\text{-}16}$ acylmethylamidodiethylammonio-1-carboxybutane; $C_{16\text{-}18}$ acylamidodimethylbetaine; $C_{12\text{-}16}$ acylamidopentanediethylbetaine; and $C_{12\text{-}16}$ acylmethylamidodimethylbetaine.

Sultaines useful in the present invention include those compounds having the formula $(R(R^1)_2N^+R^2SO^{3-})$, in which R is a $C_6$-$C_{18}$ hydrocarbyl group, each $R_1$ is typically independently $C_1$-$C_3$ alkyl, e.g. methyl, and $R^2$ is a $C_1$-$C_6$ hydrocarbyl group, e.g. a $C_1$-$C_3$ alkylene or hydroxyalkylene group.

A typical listing of zwitterionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

In an embodiment, the compositions of the present invention include a betaine. For example, the compositions can include cocoamidopropyl betaine.

Friction Reducers

Friction reducers may be present in oxidizing compositions. Examples of commonly used friction reducers include polyacrylamide polymers and copolymers. In an aspect, additional suitable friction reducers may include acrylamide-derived polymers and copolymers, such as polyacrylamide (sometime abbreviated as PAM), acrylamide-acrylate (acrylic acid) copolymers, acrylic acid-methacrylamide copolymers, partially hydrolyzed polyacrylamide copolymers (PHPA), partially hydrolyzed polymethacrylamide, acrylamide-methyl-propane sulfonate copolymers (AMPS) and the like. Various derivatives of such polymers and copolymers, e.g., quaternary amine salts, hydrolyzed versions, and the like, should be understood to be included with the polymers and copolymers described herein.

Friction reducers are combined with water and/or other aqueous fluids, which in combination are often referred to as "slick water" fluids. Slick water fluids have reduced frictional drag and beneficial flow characteristics which enable the pumping of the aqueous fluids into various gas- and/or oil-producing areas, including for example for fracturing.

In an aspect of the invention, a friction reducer is present in a use solution in an amount between about 100 ppm to 1,000 ppm. In a further aspect, a friction reducer is present in a use solution in an amount of at least about 0.01 wt-% to about 10 wt-%, preferably at least about 0.01 wt-% to about 5 wt-%, preferably at least about 0.01 wt-% to about 1 wt-%, more preferably at least about 0.01 wt-% to about 0.5 wt-%, and still more preferably at least about 0.01 wt-% to about 0.1 wt-%. Beneficially, the compositions and methods of the invention do not negatively interfere with friction reducers included in an aqueous solution.

Viscosity Enhancers

Natural and/or synthetic viscosity-increasing polymers may be present in oxidizing compositions assayed in the methods according to the invention. Viscosity enhancers may also be referred to as gelling agents and examples include guar, xanthan, cellulose derivatives and polyacrylamide and polyacrylate polymers and copolymers, and the like.

In an aspect of the invention, a viscosity enhancer is present in a use solution in an amount between about 100 ppm to 1,000 ppm. In a further aspect, a viscosity enhancer is present in a use solution in an amount of at least about 0.01 wt-% to about 10 wt-%, preferably at least about 0.01 wt-% to about 5 wt-%, preferably at least about 0.01 wt-% to about 1 wt-%, at least about 0.01 wt-% to about 2 wt-%, preferably at least about 0.01 wt-% to about 1 wt-%, preferably at least about 0.01 wt-% to about 0.5 wt-%. Beneficially, the compositions and methods of the invention do not negatively interfere with viscosity enhancer included in an aqueous solution. Without being limited to a particular theory of the invention, it is believed the reduction and/or elimination of the oxidant hydrogen peroxide from the peracid composition promotes the stability and efficacy of any variation in the amount of viscosity enhancer present in a use solution.

Corrosion Inhibitors

Corrosion inhibitors are additional molecules that may be present in oxidizing compositions. Corrosion inhibitors that may be employed in the present disclosure include the exemplary corrosion inhibitors disclosed in U.S. Pat. No. 5,965,785, U.S. patent application Ser. No. 12/263,904, GB Pat. No. 1,198,734, WO/03/006581, WO04/044266, and WO08/005,058, each incorporated herein by reference in their entireties.

In an aspect of the invention, a corrosion inhibitor is present in a use solution in an amount between about 100 ppm to 1,000 ppm. In a further aspect, a corrosion inhibitor is present in a use solution in an amount of at least about 0.0001 wt-% to about 10 wt-%, preferably at least about 0.0001 wt-% to about 5 wt-%, preferably at least about 0.0001 wt-% to about 1 wt-%, preferably at least about 0.0001 wt-% to about 0.1 wt-%, and still more preferably at least about 0.0001 wt-% to about 0.05 wt-%. Beneficially, the compositions and methods of the invention do not negatively interfere with corrosion inhibitor included in an aqueous solution.

Scale Inhibitors

Common scale inhibitors that may be employed in these types of applications include polymers and co-polymers, phosphates, phosphate esters and the like.

In an aspect of the invention, a scale inhibitor is present in a use solution in an amount between about 100 ppm to 1,000 ppm. In a further aspect, a scale inhibitor is present in a use solution in an amount of at least about 0.0001 wt-% to about 10 wt-%, at least about 0.0001 wt-% to about 1 wt-%, preferably at least about 0.0001 wt-% to about 0.1 wt-%, preferably at least about 0.0001 wt-% to about 0.05 wt-%. Beneficially, the compositions and methods of the invention do not negatively interfere with scale inhibitor included in an aqueous solution.

Additional Antimicrobial Agents

Additional antimicrobial agents may be included in oxidizing compositions. In addition to the use of peracid compositions, additional antimicrobial agents and biocides may be employed. Additional biocides may include, for example, a quaternary ammonium compound as disclosed in U.S. Pat. No. 6,627,657, which is incorporated herein by reference in its entirety. Beneficially, the presence of the quaternary ammonium compound provides both synergistic antimicrobial efficacies with peracids, as well as maintains long term biocidal efficacy of the compositions.

In another embodiment, the additional biocide may include an oxidizer compatible phosphonium biocide, such as tributyl tetradecyl phosphonium chloride. The phosphonium biocide provides similar antimicrobial advantages as the quaternary ammonium compound in combination with the peracids. In addition, the phosphonium biocide is compatible with the anionic polymeric chemicals commonly used in the oil field applications, such as the methods of the fracking disclosed according to the invention.

Additional antimicrobial and biocide agents may be employed in amounts sufficient to provide antimicrobial efficacy, as may vary depending upon the water source in need of treatment and the contaminants therein. Such agents may be present in a use solution in an amount of at least about 0.1 wt-% to about 50 wt-%, preferably at least about 0.1 wt-% to about 20 wt-%, more preferably from about 0.1 wt-% to about 10 wt-%.

Acidulants

Acidulants may be included as additional functional ingredients in oxidizing compositions. In an aspect, a strong mineral acid such as nitric acid or sulfuric acid can be used to treat water sources, as disclosed in U.S. Pat. No. 4,587,264, which is incorporated herein by reference in its entirety. The combined use of a strong mineral acid with the peracid composition provides enhanced antimicrobial efficacy as a result of the acidity assisting in removing chemical contaminants within the water source (e.g. sulfite and sulfide species). In addition, some strong mineral acids, such as nitric acid, provide a further benefit of reducing the risk of corrosion toward metals contacted by the peracid compositions according to the invention. Exemplary products are commercially available from Enviro Tech Chemical Services, Inc. (Reflex brand) and from Solvay Chemicals (Proxitane® NT brand).

Acidulants may be employed in amounts sufficient to provide the intended antimicrobial efficacy and/or anticorrosion benefits, as may vary depending upon the water source in need of treatment and the contaminants therein. Such agents may be present in a use solution in an amount of at least about 0.1 wt-% to about 50 wt-%, preferably at least about 0.1 wt-% to about 20 wt-%, more preferably from about 0.1 wt-% to about 10 wt-%.

Catalase and Peroxidase Enzyme

A catalase or peroxidase enzyme may be used to reduce and/or eliminate the concentration of hydrogen peroxide in an antimicrobial peracid composition. The enzymes catalyze the decomposition of hydrogen peroxide to water and oxygen. Beneficially, the reduction and/or elimination of hydrogen peroxide (strong oxidizer) results in other additives for a water treatment source (e.g. water source) not being degraded or rendered incompatible. Various additives used to enhance or modify the characteristics of the aqueous fluids used in well drilling, recovery and production applications are at risk of degradation by the oxidizing effects of hydrogen peroxide. These may include for example, friction reducers and viscosity enhancers used in commercial well drilling, well completion and stimulation, or production applications Various sources of catalase enzymes may be employed according to the invention, including: animal sources such as bovine catalase isolated from beef livers; fungal catalases isolated from fungi including *Penicillium chrysogenum*, *Penicillium notatum*, and *Aspergillus niger*; plant sources; bacterial sources such as *Staphylococcus aureus*, and genetic variations and modifications thereof. In an aspect of the invention, fungal catalases are utilized to reduce the hydrogen peroxide content of a peracid composition. Catalases are commercially available in various forms, including liquid and spray dried forms. Commercially available catalase includes both the active enzyme as well as additional ingredients to enhance the stability of the enzyme. Some exemplary commercially available catalase enzymes include Genencor CA-100 and CA-400, as well as Mitsubishi Gas and Chemical (MGC) ASC super G and ASC super 200, and Optimase CA 400L from Genecor International. Additional description of suitable catalase enzymes are disclosed and herein incorporated by reference in its entirety from U.S. Patent Publication No. 2009/0269324.

In an aspect of the invention, catalase enzymes have a high ability to decompose hydrogen peroxide. Beneficially, the reduction or elimination of hydrogen peroxide from oxidizing compositions obviates the various detriments caused by oxidizing agents. In particular, the use of catalase with the peracids compositions provides enhanced antimicrobial benefits without causing the damage associated with conventional oxidizing agents (e.g. peracetic acid, hypochlorite or hypochlorous acid, and/or chlorine dioxide), such as corrosion.

Peroxidase enzymes may also be employed to decompose hydrogen peroxide from a peracid composition. Although peroxidase enzymes primarily function to enable oxidation of substrates by hydrogen peroxide, they are also suitable for effectively lowering hydrogen peroxide to peracid ratios in compositions. Various sources of peroxidase enzymes may be employed according to the invention, including for example animal sources, fungal peroxidases, and genetic variations and modifications thereof. Peroxidases are commercially available in various forms, including liquid and spray dried forms. Commercially available peroxidases include both the active enzyme as well as additional ingredients to enhance the stability of the enzyme.

In some embodiments, the catalase or peroxidase enzyme is able to degrade at least about 50% of the initial concentration of hydrogen peroxide in a peracid composition. Preferably, the enzyme is provided in sufficient amount to reduce the hydrogen peroxide concentration of a peracid composition by at least more than about 50%, more preferably at least about 60%, at least about 70%, at least about 80%, at least about 90%. In some embodiments, the enzyme reduces the hydrogen peroxide concentration of a peracid composition by more than 90%. In an aspect of the invention, the enzymes are suitable for use and have a tolerance to a wide range of temperatures, including the temperatures ranges in water treatment applications which may range from about 0-180° C. A suitable catalase enzyme will maintain at least 50% of its activity under such storage and/or application temperatures for at least about 10 minutes, preferably for at least about 1 hour.

In a further aspect of the invention, the catalase or peroxidase enzymes described herein have a tolerance to pH ranges found in water treatment applications. Acetic acid levels (or other carboxylic acid) in a water treatment application can widely range in parts per million (ppm) of acetic or other carboxylic acid. The solutions may have a corresponding range of pH range from greater than 0 to about 10. A suitable catalase or peroxidase enzyme will maintain at least about 50% of its activity in such solutions of acetic or other carboxylic acid over a period of about 10 minutes.

In an aspect of the invention, a catalase or peroxidase enzyme is present in a use solution of the water treatment and peracid composition in sufficient amounts to reduce the concentration of hydrogen peroxide from the peracid composition by at least 50% within about 10 minutes, preferably within about 5 minutes, preferably within about 2 to 5 minutes, more preferably within about 1 minute. The ranges of concentration of the enzymes will vary depending upon the amount of time within which 50% of the hydrogen peroxide from the peracid composition is removed. In certain aspects of the invention, a catalase or peroxidase enzyme is present in a use solution composition including the water source to be treated in amounts between about 1 ppm and about 1,000 ppm, preferably between about 5 ppm and 500 ppm, and more preferably between about 10 ppm and about 100 ppm.

Fluorometric Detection

Any fluorometer can be used on the samples prepared according to the invention. In general, the fluorometer can measure intensity of fluorescent emission from a sample (e.g., a chemical solution, such as an antimicrobial or cleaning product) having a substance of interest (e.g., dipicolinic acid). The fluorometer can calculate concentration of the substance in the sample, and display the determined concentration to a user. The user can then perform any desired actions based on the determined concentration, such as, for example, adding more of the substance in order to increase the concentration of the substance. If the fluorometer determines that the concentration is lower or higher than a threshold concentration, the user can dispense more or less of the substance. Additionally, the fluorometer can be operatively coupled to an out-of-product sensor. In certain embodiments, when the concentration of the substance is below a pre-determined threshold, the fluorescence emitted by the substance may be at a lower intensity. At this point, the out-of-product sensor can alert the user that the concentration of the substance has reached below a pre-determined threshold. The signal can be a visual, audio signal, or any other type of signal known in the art. Accordingly, the user can ensure that sufficient quantity and/or concentration of cleaning, antimicrobial, sanitizing and/or disinfecting solution, or other substances of interest is present to achieve the desired effect (cleanliness, reduction in microorganisms, heat resistance, product stability, lubrication, etc.).

The basic operation of a fluorometer is well known, and accordingly, various details are omitted here for conciseness and clarity. The fluorometer can calculate a concentration of a particular substance in a sample based on fluorescent properties of the substance. As will be described in more detail herein, the fluorometer includes an excitation source that emits electromagnetic radiation at one or more selected wavelengths, or continuously within a wavelength range. When the substance of interest is exposed to electromagnetic radiation at one or more selected wavelengths, (e.g., within a wavelength range), it may cause excitation of electrons in certain molecules of the substance and induce them to emit electromagnetic radiation. The emitted electromagnetic radiation can be of a different energy (i.e., at another wavelength range) from the electromagnetic radiation emitted by the excitation source. The electromagnetic radiation emitted by the substance can then be converted into an electrical signal. The electrical signal can indicate the intensity of fluorescent emissions. The concentration of the substance can then be determined based on a known relationship between the intensity of the fluorescent emissions and the concentration of the substance (e.g., via a calibration).

Certain embodiments of the invention include a fluorometer for measuring fluorescence of a sample. The fluorometer can include a housing, a controller supported by the housing, and a sensor head. The sensor head can include an emitter module and a detector module operatively coupled to the controller. The emitter module can include an excitation source configured for emitting electromagnetic radiation at one or more wavelengths to induce fluorescence in the sample. The emission of the electromagnetic radiation can be directed along a first beam path. The sensor head can include an excitation filter for transmitting electromagnetic radiation within a first wavelength range toward the sample. The excitation filter can be supported by an excitation filter holder. The excitation filter holder can define an aperture for passage of electromagnetic radiation. The excitation filter holder can support the excitation filter such that the excitation filter permits passage of filtered electromagnetic radiation through the aperture and towards the sample such that the first beam path defines a trajectory of electromagnetic radiation from the excitation source to the excitation filter, via the aperture and toward the sample. The detector module can detect fluorescence emitted by the sample. The fluorometer displays the concentration of the substance in the sample determined by the controller, based on the measured fluorescence.

In some embodiments, the fluorometer includes a first focusing apparatus and a second focusing apparatus. The first focusing apparatus and the second focusing apparatus can be housed in the housing proximate the sensor head. The first focusing apparatus can direct electromagnetic radiation originating from the excitation source and transmitted by the excitation filter towards the sample. The second focusing apparatus can direct fluorescence originating from the sample toward the detector module.

In some embodiments, the aperture can be positioned asymmetrically relative to the first beam path such that the aperture passes an asymmetrical portion of the electromagnetic radiation in the first beam path and the excitation filter holder blocks passage of a corresponding asymmetrical portion of the electromagnetic radiation in the first beam path. The blocked passage of the corresponding asymmetrical portion of the electromagnetic radiation in the first beam path can reduce the amount of electromagnetic radiation oriented directly from the emitter module to the detector module. In some embodiments, the aperture is of semi-circular cross-section. In some embodiments, the aperture is shaped by obstructing at least a portion of a circular opening. In some embodiments, the aperture is shaped to prevent electromagnetic radiation passing through the first focusing apparatus from being directed toward the second focusing apparatus.

A number of variations and specific details of this general process are contemplated for embodiments of the invention involving fluorometers. In one example the concentration of water treatment products or solutions may be determined. In another example, the substance of interest may be any chemical solution. Examples include, but are not limited to, biocides such as pesticide and antimicrobial products, anti-corrosion, antiscaling, and antifouling products, disinfectants, and other cleaning products, detergents, additives, surfactants, lubricants, antimicrobial agents, solvents, hydrotropes, antiredeposition agents, dyes, corrosion inhibitors, acids, alkaline solutions, salt solutions, and bleaching additives. These compounds can be incorporated into products like ware-washing detergents, rinse aids, laundry detergents, clean-in-place cleaners, antimicrobials, floor coatings, meat, poultry and seafood carcass treatments, pesticides, vehicle care compositions, water care compositions, pool and spa compositions, aseptic packaging compositions, bottle washing compositions, and the like. Examples of some of these compounds and corresponding applications can be found in U.S. Pat. No. 7,550,746 assigned to the assignee of the instant application, the disclosure of which is herein incorporated by reference.

Thus, embodiments of the invention are disclosed. Although the present invention has been described in considerable detail with reference to certain disclosed embodiments, the disclosed embodiments are presented for purposes of illustration and not limitation and other embodiments of the invention are possible. One skilled in the art will appreciate that various changes, adaptations, and modifications may be made without departing from the spirit of the invention.

EXAMPLES

Example 1

Sample Testing with No Reducing Agent

For each of the tests below, a fluorimeter was used with an emission at 272 nm to cause fluorescence at 545 nm which is then calibrated to determine the amount of DPA present. Sample preparation is as disclosed and includes the addition of 0.011M $TbCl_3$. Tests were run measuring a sample of peroxycarboxylic acid stabilized with DPA to determine concentration of DPA with varying levels of DPA. The DPA was complexed with Terbium chloride to generate a measurable excitation signal of the DPA;$TbCl_3$ complex. The results are shown graphically in FIG. 1 and are reported in Table 1 below. The testing was done with a sample containing 400 ppm DPA. At a 1:200 product dilution, one can see that the concentration determined is not linear and the oxidizing agent (Peroxyacetic acid-POAA) is absorbing the excitation light. The sample is too concentrated.

TABLE 1

| Linearity - varying aliquot of product, keeping same aliquot of TbCl3 | | | | | | |
|---|---|---|---|---|---|---|
| Working Concentration | Sample Size, mL/L | 0.0024 TbCl3, mL/L | Reading, ppm | Sensitivity ppm/mL | Theo ppm | % Recovery |
| 20 | 1.00 | 5 | 99 | 99.000 | 77.00 | 128.57 |
| 40 | 2.00 | 5 | 184 | 92.000 | 154.00 | 119.48 |
| 60 | 3.00 | 5 | 273 | 91.000 | 231.00 | 118.18 |
| 80 | 4.00 | 5 | 332 | 83.000 | 308.00 | 107.79 |
| 100 | 5.00 | 5 | 385 | 77.000 | 385.00 | Control |
| 120 | 6.00 | 5 | 410 | 68.333 | 462.00 | 88.74 |
| 140 | 7.00 | 5 | 430 | 61.429 | 539.00 | 79.78 |
| 160 | 8.00 | 5 | 431 | 61.571 | 616.00 | 69.97 |

Median 80.000
3*% RSD 3.788
3.030
Upper Limit 83.030
Lower Limit 76.970

The test was also run varying the amount of TbCl3 with similar non-linear results. See Table 2 below.

TABLE 2

Linearity - varying aliquot of both the product and the TbCl3

| Working Concentration | Sample Size, mL/L | 0.0024 TbCl3, mL/L | Reading, ppm | Sensitivity ppm/mL | Theo ppm | % Recovery |
|---|---|---|---|---|---|---|
| 20 | 1.00 | 1 | 98 | 98.000 | 77.00 | 127.27 |
| 40 | 2.00 | 2 | 179 | 89.500 | 154.00 | 116.23 |
| 60 | 3.00 | 3 | 250 | 83.333 | 231.00 | 108.23 |
| 80 | 4.00 | 4 | 324 | 81.000 | 308.00 | 105.19 |
| 100 | 5.00 | 5 | 385 | 77.000 | 385.00 | Control |
| 120 | 6.00 | 6 | 418 | 69.667 | 462.00 | 90.48 |
| 140 | 7.00 | 7 | 460 | 65.714 | 539.00 | 85.34 |
| 160 | 8.00 | 8 | 500 | 71.429 | 616.00 | 81.17 |

Median 79.000
3*% RSD 3.788
2.993
Upper Limit 81.993
Lower Limit 76.007

As can be seen, varying both the sample size of product and the $TbCl_3$ at a product dilution of dilution of 1:200, the response was non-linear, indicating that the sample is too concentrated, absorbance too high. Readings of the amount of fluorescence did not correlate in a linear fashion with the amount of DPA present.

Figure 2:
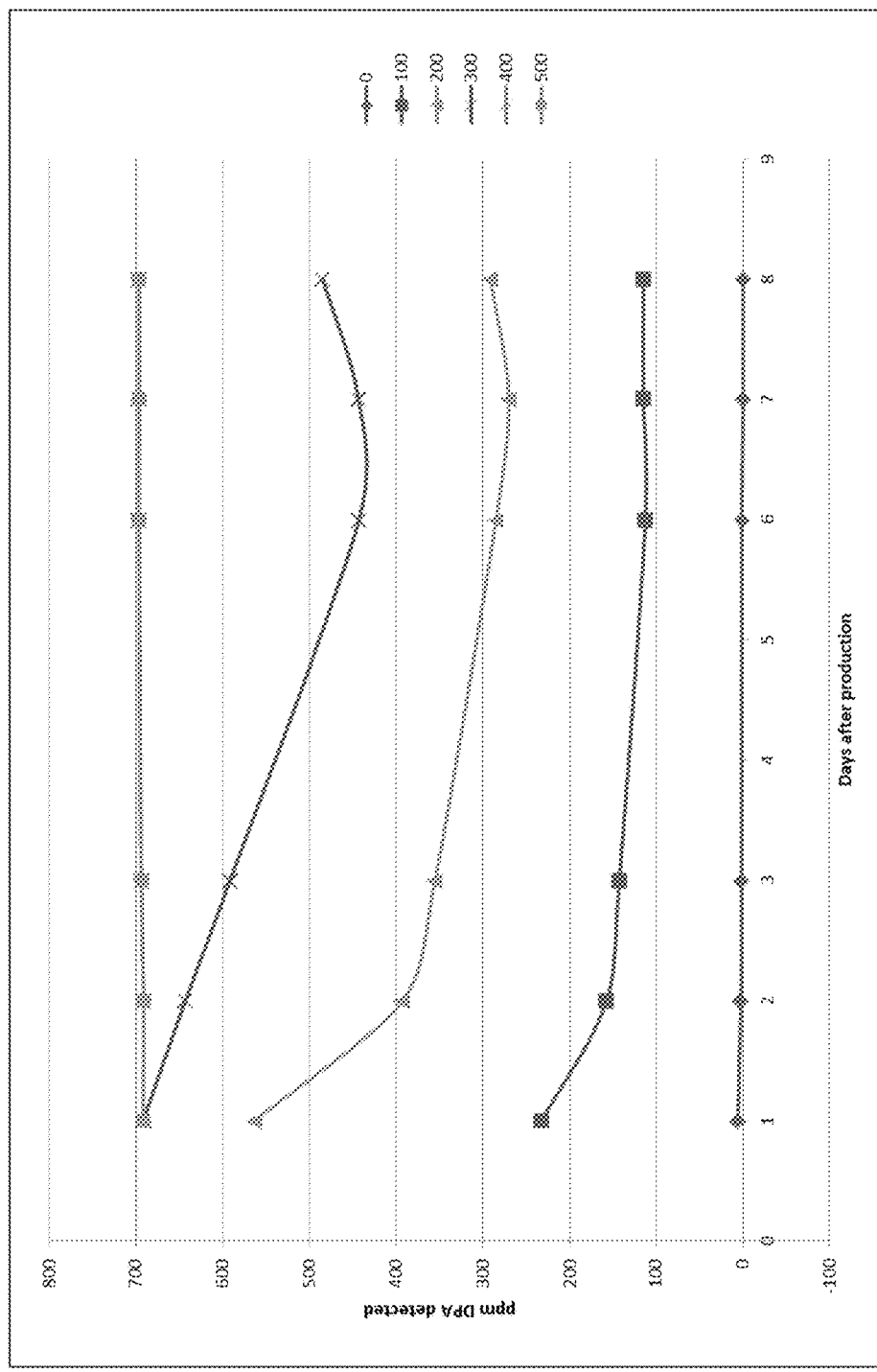
FIG. 2 is a graph showing the detection of DPA during peracid equilibrium with varying levels of DPA at a 1:200 dilution of product sample.

Next, tests were run on at a dilution of 1:200 of peroxycarboxylic acid composition stabilized with DPA with varying the levels of DPA as the peroxcycarboxylic acid solution equilibrates over time. The Results are shown in FIG. 2. Data for FIG. 2 were measured using samples prepared from Table 3 below. DPA concentration always 400 ppb=400 ppm/1000.

Product dilutions 2000 for 50% point, 1000 for 100% point, 500 for 200% point, 250 for 400% point.

TABLE 3

| | Dilution | | | | 1000x | | | |
|---|---|---|---|---|---|---|---|---|
| Stock DPA | | | | Calibration solutions | | | | |
| Read, ppm | DPA, ppm | TbCl3, M | Vol ml | TbCl3 ml | Sample ml | Thio ml | DPA, ml | H2O, ml |
| 400 | 0.4 | 0.000012 | 100 | 25 | 10 | 0 | 2.5 | 62.5 |
| 400 | 0.4 | 0.000012 | 100 | 25 | 7.5 | 0 | 2.5 | 65 |
| 400 | 0.4 | 0.000012 | 100 | 25 | 5 | 0 | 2.5 | 67.5 |
| 400 | 0.4 | 0.000012 | 100 | 25 | 2.5 | 0 | 2.5 | 70 |
| 400 | 0.4 | 0.000012 | 100 | 25 | 1.25 | 0 | 2.5 | 71.25 |
| 400 | 0.4 | 0.000012 | 100 | 25 | 0.625 | 0 | 2.5 | 71.875 |
| 400 | 0.4 | 0.000012 | 100 | 25 | 0 | 0 | 2.5 | 72.5 |
| Total | | | 600 | 150 | 16.875 | 0 | 15 | 418.125 |
| Nominal dilution | 40 | | | | | | | |

TbCl3 10 times relatively for first samples with DPA dilution 1000 times
Sample is a concentrate diluted 25 times to have 4%

From the results one can see that as more POAA generates over time, more signal is absorbed and the linearity decreases.

Figure 3:
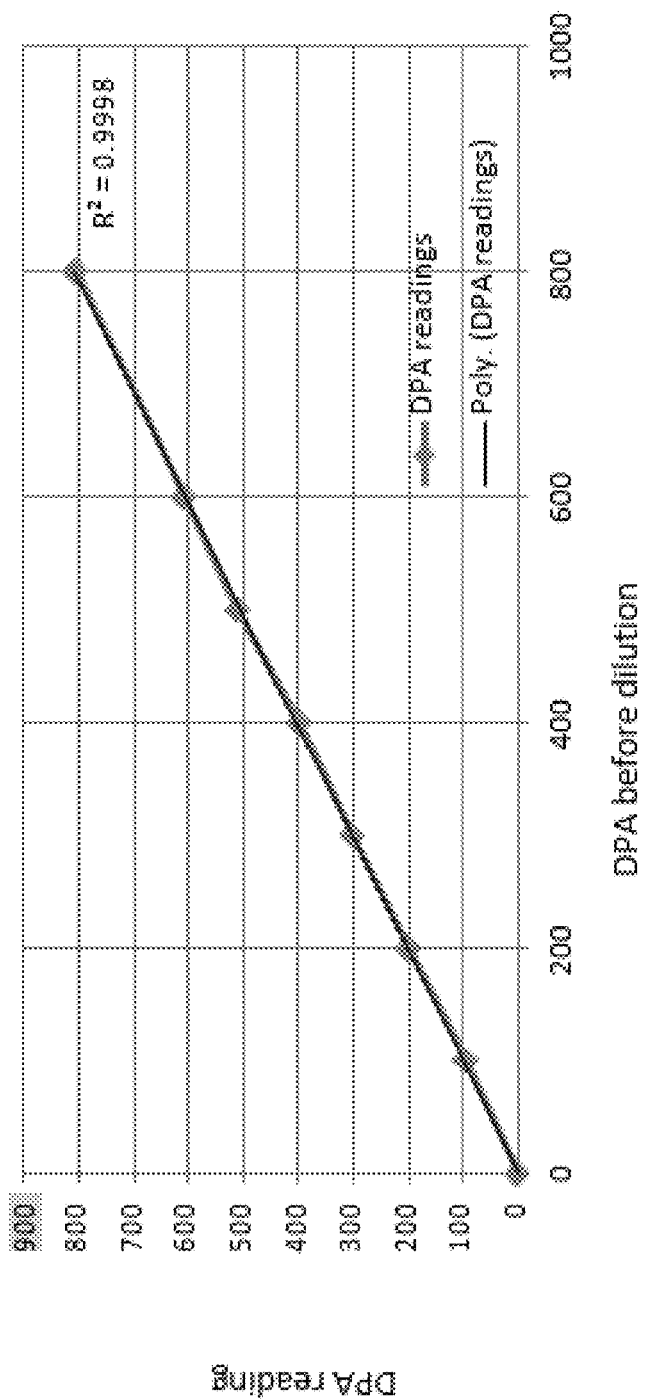
FIG. 3 is a graph showing fluorometer readings of DPA for 1:100 dilution of peracid sample and $TbCl_3$.

Next the sample dilution was extended from 1:200 to 1:1000. The data is shown in FIG. 3. At this level of dilution we see a linear response, but this was for a product that was already equilibrated, (no varying levels of POAA). The test was also run by different people with similar more linear results, see Table 4 below:

TABLE 4

| | Technician 1 | Technician 2 |
|---|---|---|
| Sample 1 | 391.7 | 391.7 |
| Sample 2 | 391.0 | 396.2 |
| Sample 3 | 392.1 | 389.3 |
| Sample 4 | 392.5 | 394.7 |
| Sample 5 | 391.8 | 395.4 |
| Mean | 391.8 | 393.5 |
| Std Deviation | 0.55 | 2.88 |
| % RSD | 0.14 | 0.73 |

Figure 4:
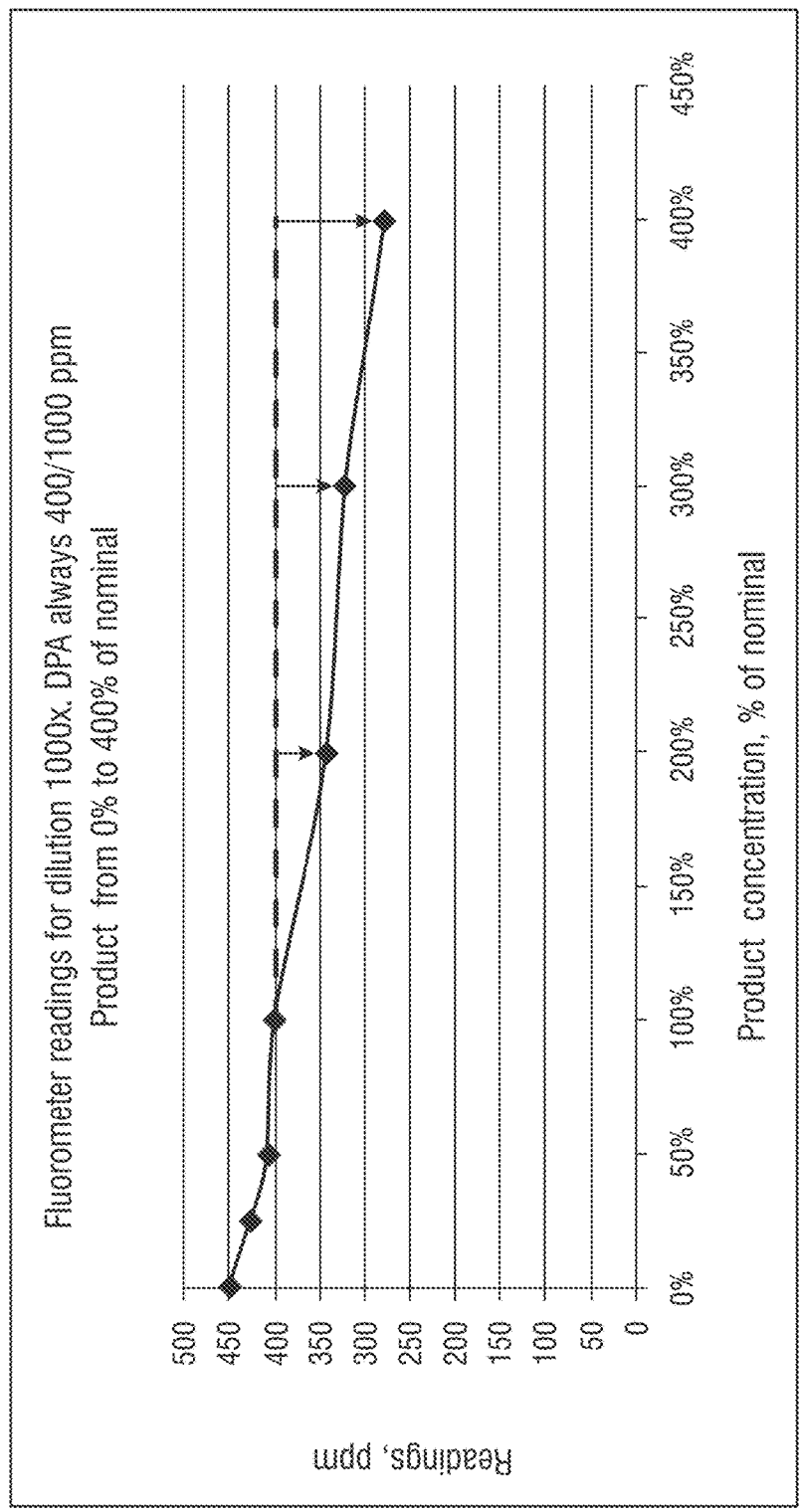
FIG. 4 is a graph showing the variations of readings for 400 ppm DPA at 1:1000 dilution with increasing peracid concentration. The ppm readings decrease as the fluorescence is dampened by increasing amounts of peracid. Dotted line shows a desired linear relationship.
Figure 5:
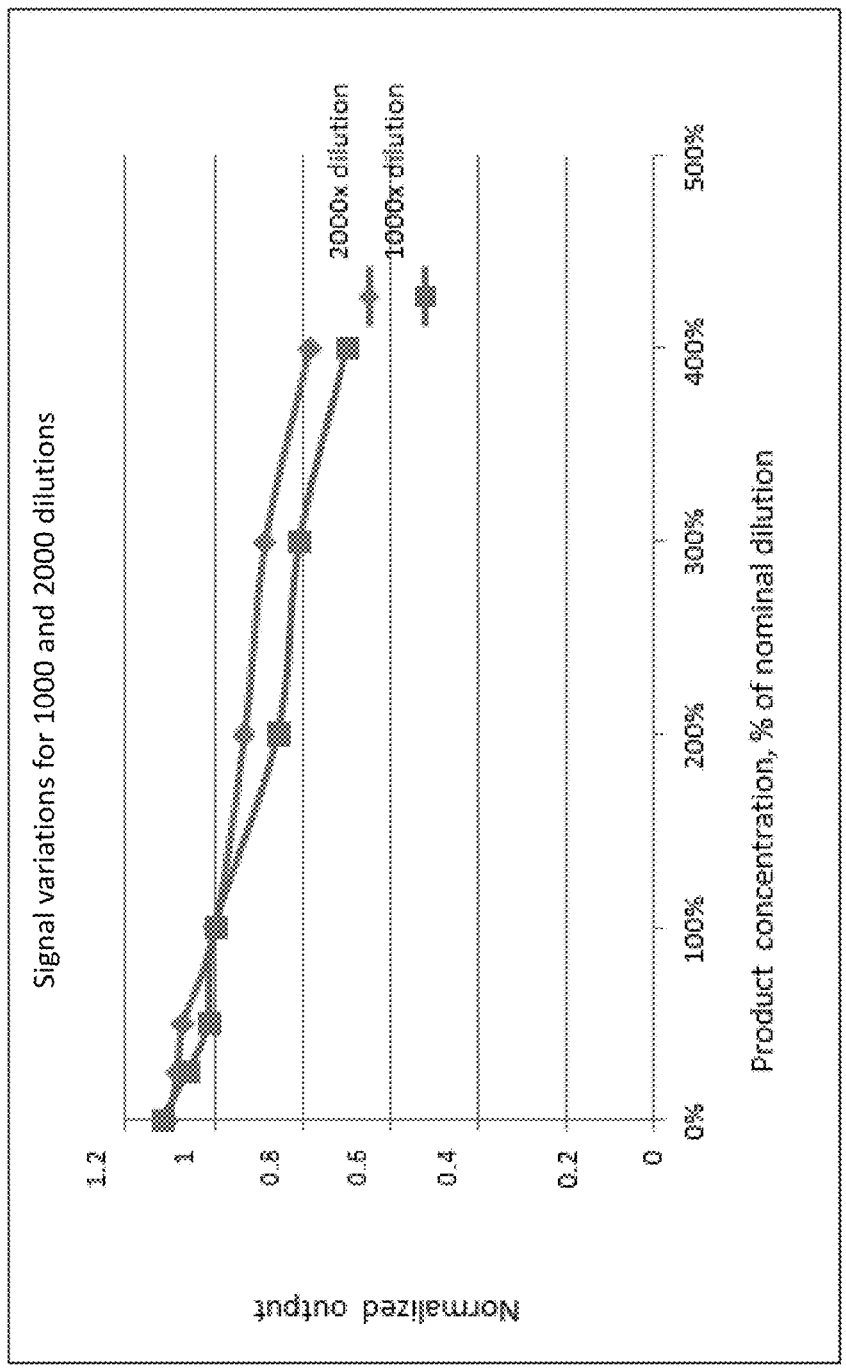
FIG. 5 is a graph showing the test run at 1:1000 and 1:2000 dilutions of sample, one can still see the dampening of fluorescence even at the much higher dilution

In FIG. 4 one can see that at 1:000 dilution when there is a variable POAA concentration, the peracid effect continues and readings for DPA ppm are still variable and decrease as increasing amounts of POAA dampen the fluorescence signal. In FIG. 5, dilution was increased to 1:2000 and compared to 1:1000. Here again even at the 2000 dilution, POAA dampens the signal, although the 2000 dilution is more linear.

Figure 6:
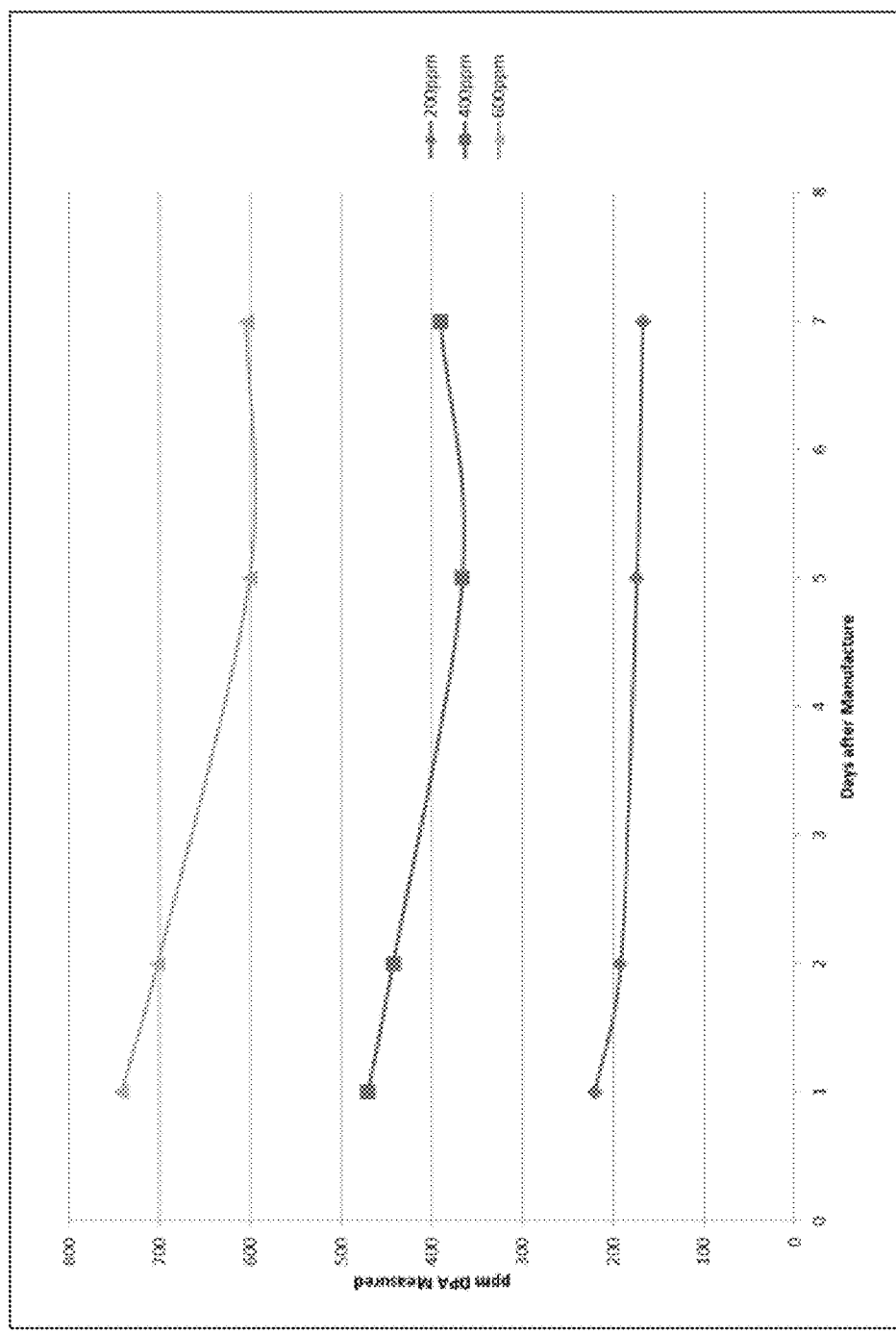
FIG. 6 is a graph showing the measurement of DPA at 200, 400 and 600 ppm as the peracid solution equilibrates over time without thiosulfate addition at a 1:1000 dilution.

In FIG. 6 comparisons of fluorescence were measured over time as the sample equilibrates. One can see that as more POAA is over time the signal is dampened even with different amounts of DPA.

Example 2

Use of Reducing Agent to Eliminate Interference from Oxidizers

Applicants discovered that use of a reducing agent, such as thiosulfate can eliminate the interference from POAA. According to the invention, sodium thiosulfate reacts with peroxyacetic acid (POAA) to form acetic acid, sodium sulfate and elemental sulfur. The sodium thiosulfate also reacts with hydrogen peroxide ($H_2O_2$) to form water, sodium sulfate and sulfuric acid.

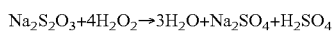

$Na_2S_2O_3 + 4H_2O_2 \rightarrow 3H_2O + Na_2SO_4 + H_2SO_4$

$Na_2S_2O_3 + CH_3CO_3H \rightarrow HC_2H_3O_2 + Na_2SO_4 + 1/8 S_8$

The actives concentration constantly changes during equilibrium, but with the addition of sodium thiosulfate, the solution becomes stable and constant.

Figure 7:
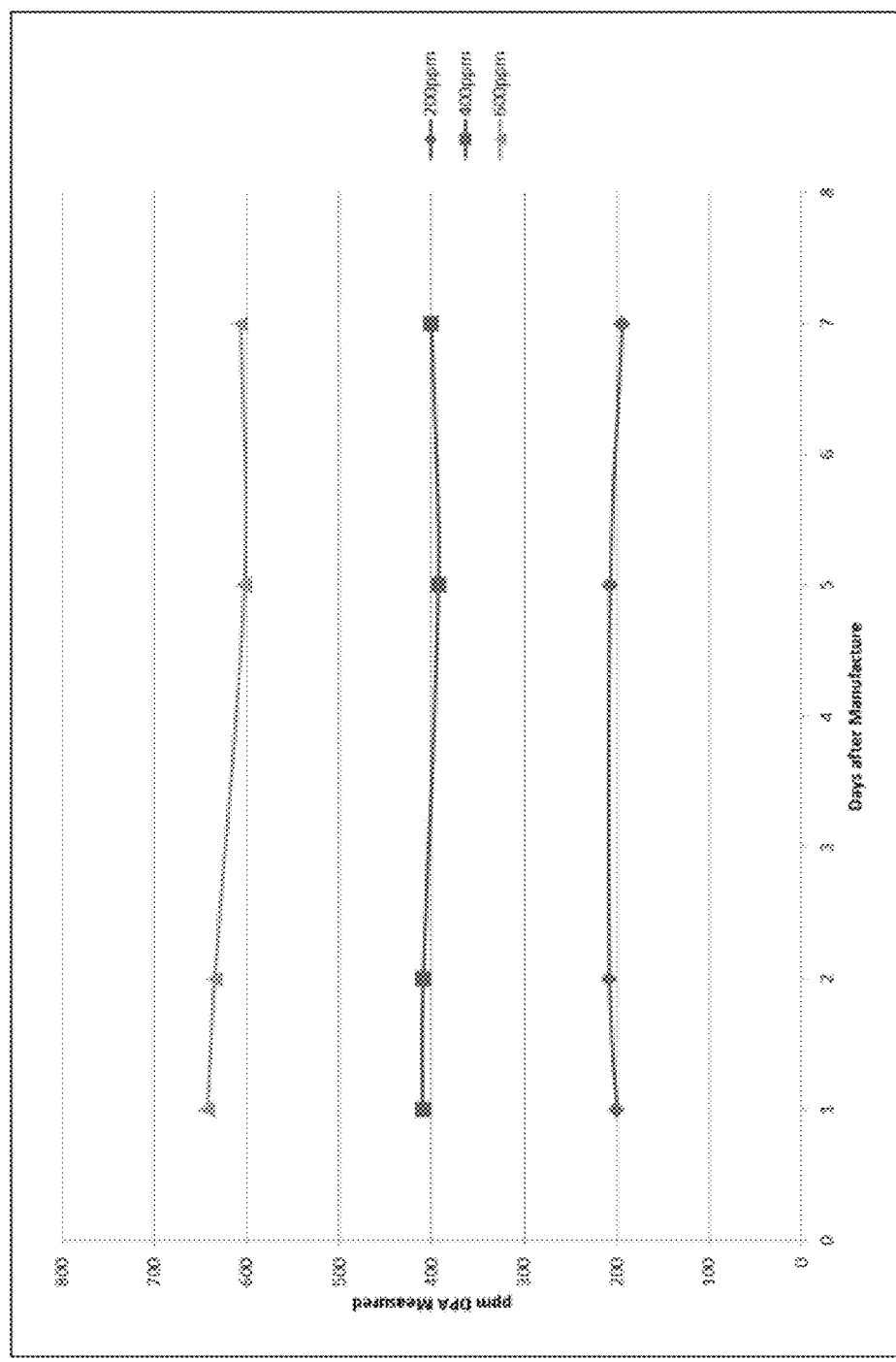
FIG. 7 is a graph showing the 200, 400, and 600 ppm DPA as the peracid solution equilibrates over time with the addition of thiosulfate at a 1:1000 solution.

FIG. 7 shows that with the additional of 100 mL of 0.1N thiosulfate, to the sample preparation and testing as done in FIG. 6. One can see that with the addition of thiosulfate the graph is more linear at 200 ppm, 400 ppm, and 600 ppm DPA.

The sample preparation for FIG. 7 was then repeated 6 different times and one can see that the linearity is excellent and the average percent recovery is excellent at 99.79%. Results are shown in Table 5

TABLE 5

| Lab Batch | Target DPA Conc. (ppm) | Theoretical DPA Conc. (ppm) | Meter Reading (ppm) | Percent Recovery |
|---|---|---|---|---|
| 1 | 100 | 100.9 | 103.30 | 102.38 |
| 2 | 200 | 200.2 | 205.50 | 102.65 |
| 3 | 300 | 302.0 | 296.50 | 98.18 |
| 4 | 400 | 401.2 | 391.70 | 97.63 |
| 5 | 500 | 504.7 | 509.70 | 100.99 |
| 6 | 600 | 609.9 | 591.10 | 96.92 |

Results are within 5% of each analyst

Figure 8:
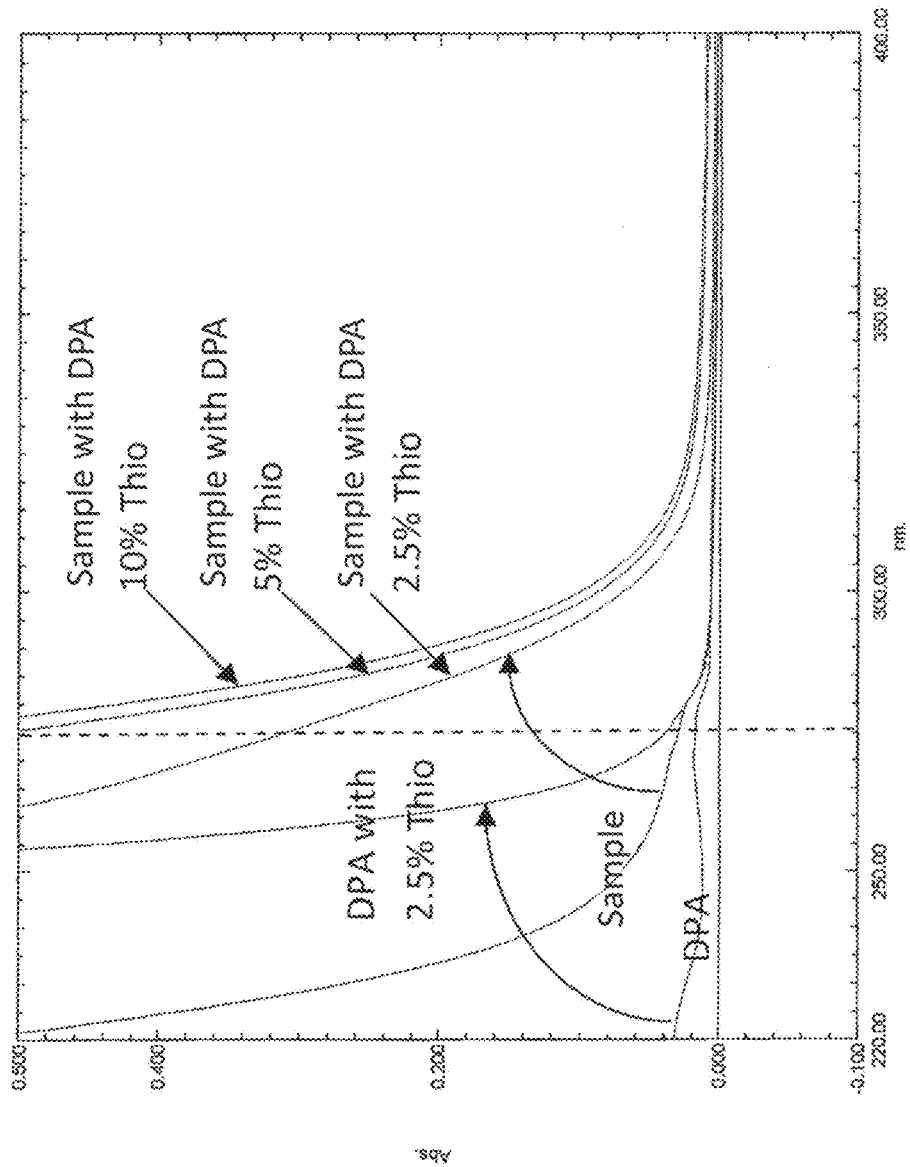
FIG. 8 is a graph showing the fluorometric readings at different concentrations of thiosulfate.

Amounts of thiosulfate addition were then tested and fluorimeter measurements were taken with DPA alone, peracid alone, DPA with 2.5% thiosulfate, and peracid with DPA and 2.5% thiosulfate, peracid with DPA and 5% thiosulfate, and finally peracid with DPA and 10% thiosulfate. (0.1N Thiosulfate was added). The results are shown in FIG. 8 and Table 4 below. One can see that thiosulfate must be between 2.5% and 5% for detection within the linear range.

One can see the response is lowered 20× with 0.01N thiosulfate and absorption above 5% may indicate operation outside of linear range. Excitation is at 272 nm.

TABLE 6

| Optical density (OD) for 10 mm cell | |
|---|---|
| DPA | 0.003 |
| Peracid with DPA | 0.017 |
| Peracid with DPA and 2.5% of thiosulfate | 0.310 |
| Peracid with DPA and 5.0% of Thiosulfate | 0.510 |
| Peracid with DPA and 10.0% of Thiosulfate | 0.610 |

Figure 9:
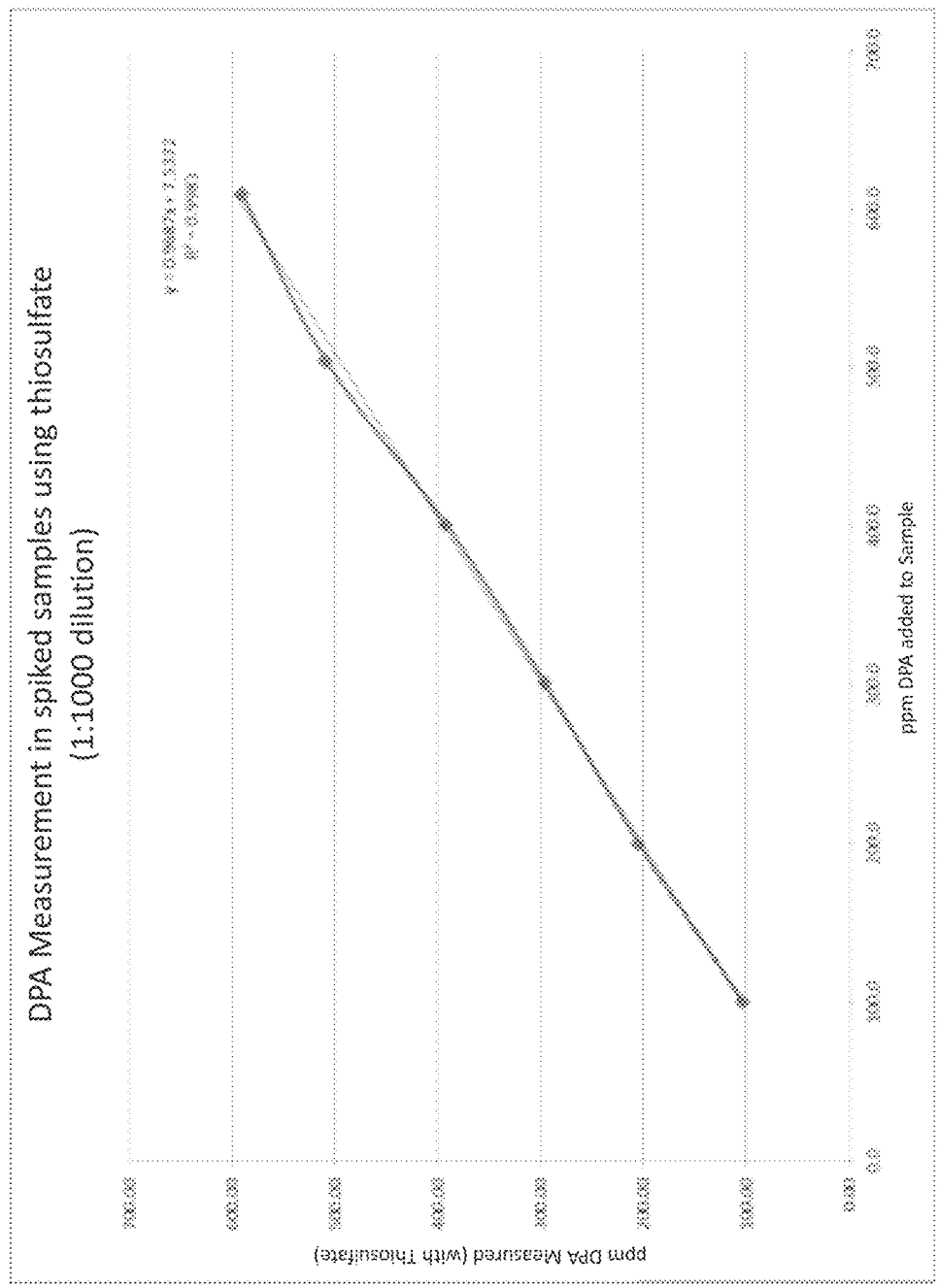
FIG. 9 is a graph of the sample readings of ppm DPA as determined with 1:1000 dilution and addition of thiosulfate.
Figure 10:
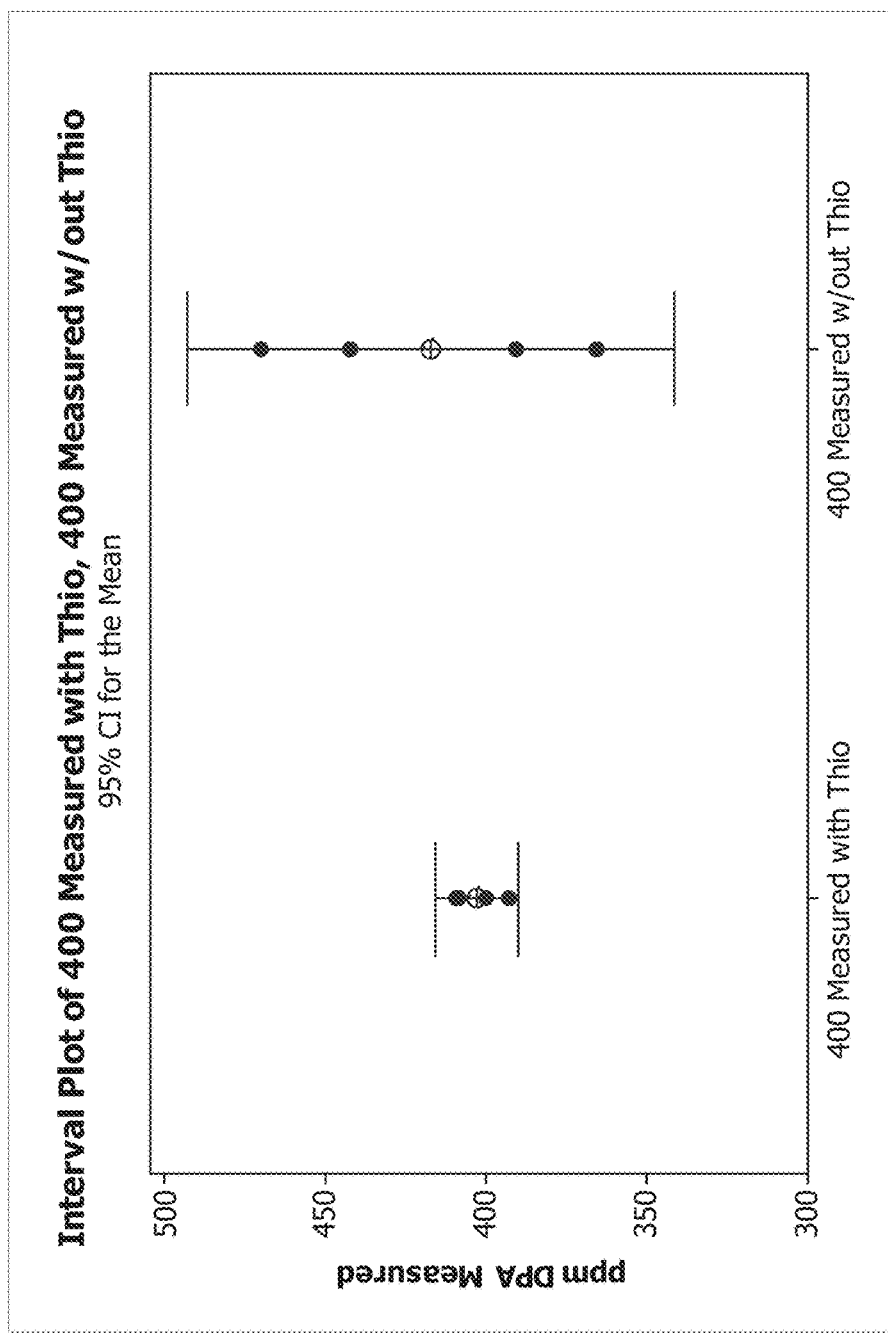
FIG. 10 is a graph showing 400 ppm DPA as measured with thiosulfate addition and without thiosulfate addition as peracid concentration increases over time. Measurements are at the 1, 2, 5, and 7 days.

FIG. 9 shows the readings with measured DPA at 1:1000 dilution. One can see that at 1:1000 dilution, and addition of thiosulfate, the response observed is almost perfectly linear. In FIG. 10, samples with 400 ppm DPA with and without thiosulfate addition, one can see that the during days 1-7 during equilibrations demonstrates that that with thiosulfate there is significantly less variability in the measurements even with varying amounts of POAA present as the samples equilibrates. Measurements taken at days 1, 2, 5, and 7.

Example 3

Sample Test Protocol

Molecules can absorb light in liquid solutions, thereby promoting ground state electrons into higher energy states. Fluorescence occurs for about 10 nanoseconds or less when a photon of light is released as the electron returns to the ground state. Fluorescence is dependent on numerous factors, including temperature and pH. Changes to these parameters can bias the final result. When $TbCl_3$ is added to DPA in solution, it binds in a 1:3 ratio to form a complex. The $TbCl_3$ needs to be in a small amount of excess to ensure that it binds all available DPA. The complex that is formed has an excitation wavelength of 272 nm, and an Emission wave length at 545 nm. The test was run with an aqueous solution of 400 ppm DPA. Some molecules will absorb light in these wave lengths, which will interfere with the fluorescence signal, giving a result with a low bias. Significantly different levels of peracid in a sample will yield different results for the same concentration of DPA. The addition of sodium thiosulfate to the sample test solution is used to neutralize peracid and peroxide species in the formula, mitigating the effects of the peracid equilibrium on the fluorescence test. Pre- and post-equilibration readings can be taken with the thiosulfate addition.

Fluorometer, capable of excitation/emission at 272/545 nm
Procedure: All samples should be run at approximately room temperature
1. Add approximately 800 mL DI water to an IL volumetric flask.
2. Using a graduated cylinder, add 100 mL 0.1N sodium thiosulfate to the flask.
3. Weigh or aliquot desired amount of peracid product (as specified by product bill of quality) into the 1 L flask. Aliquot 1 mL of 0.011M $TbCl_3$, to the 1 L flask.
4. Bring the flask to volume and mix for thirty minutes (+/−5 minutes)
6. Assay fluorometrically, by measuring and recording the fluorescence.

What is claimed is:

1. A method of detecting a target analyte in a sample of an oxidizing composition comprising:
    adding to said sample an effective amount of a reducing agent to form a sample solution and so that a peracid and hydrogen peroxide are reduced; and
    assaying said sample solution with fluorescence detection to determine the concentration of the target analyte,
    wherein said oxidizing composition comprises the peracid and hydrogen peroxide;
    wherein the reducing agent neutralizes peracid and hydrogen peroxide in the sample and mitigates effects of the peracid and hydrogen peroxide on the fluorescence detection;
    wherein the reducing agent is not an enzyme; and
    wherein the target analyte exhibits fluorescence.

2. The method of claim 1 wherein the oxidizing composition is a peracid composition.

3. The method of claim 1 wherein said analyte is substituted or nonsubstituted mono, di or tri picolinic acid.

4. The method of claim 3 wherein said picolinic acid has the following formula:

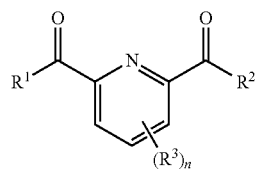

wherein $R^1$ is OH or $-NR^{1a}R^{1b}$, wherein $R^{1a}$ and $R^{1b}$ are independently hydrogen or $(C_1-C_6)$ alkyl;
$R^2$ is OH or $-NR^{2a}R^{2b}$, wherein $R^{2a}$ and $R^{2b}$ are independently hydrogen or $(C_1-C_6)$ alkyl;
each $R^3$ is independently $(C_1-C_6)$alkyl, $(C_2-C_6)$alkenyl or $(C_2-C_6)$ alkynyl; and n is a number from zero to 3;
or a salt thereof;
or a compound having the following Formula:

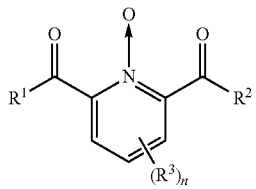

wherein
R$^1$ is OH or —NR$^{1a}$R$^{1b}$, wherein R$^{1a}$ and R$^{1b}$ are independently hydrogen or (C$_1$-C$_6$)alkyl; R$^2$ is OH or —NR$^{2a}$R$^{2b}$, wherein R$^{2a}$ and R$^{2b}$ are independently hydrogen or (C$_1$-C$_6$)alkyl; each R$^3$ is independently (C$_1$-C$_6$)alkyl, (C$_2$-C$_6$)alkenyl or (C$_2$-C$_6$)alkynyl; and
n is a number from zero to 3;
or a salt thereof.

5. The method of claim 1 wherein said reducing agent is one or more of a sulfite, phosphite, hypophosphite, phosphorous acid, oxalic acid, formic acid, ascorbic acid, or a thiosulfate.

6. The method of claim 1, wherein said reducing agent is a sulfite.

7. The method of claim 1, wherein said reducing agent is a thiosulfate.

8. The method of claim 3 further comprising the step of treating said sample with an effective amount of terbium chloride so that said terbium chloride forms a complex with picolinic acid in said sample.

9. The method of claim 1 wherein said oxidizing composition is a bleaching composition.

10. The method of claim 1 wherein said fluorescence detection is by a hand held fluorimeter.

11. The method of claim 1 further comprising the step of:
diluting said sample solution 1:1000 with water.

12. A method of determining the concentration of a picolinic acid in a sample of an oxidizing formulation, comprising:
pretreating said sample with an effective amount of terbium chloride so that said picolinic acid is complexed with terbium chloride;
pretreating said sample with an effective amount of a reducing agent to that a peracid and hydrogen peroxide in said sample are reduced;
subjecting said sample to an electromagnetic radiation from an excitation source at wavelengths that induce fluorescence in said picolinic acid;
detecting the fluorescence emitted by the picolinic acid using a predetermined relationship between fluorescence emitted and the concentration of the picolinic acid,
wherein the reducing agent neutralizes peracid and hydrogen peroxide in the sample and mitigates effects of the peracid and hydrogen peroxide on the fluorescence detection;
wherein the reducing agent is not an enzyme; and
wherein the oxidizing formulation comprises the peracid and hydrogen peroxide.

13. The method of claim 12, wherein said pretreating step with an effective amount of terbium chloride includes adding terbium chloride to said picolinic acid in a ratio of about 1:3.

14. The method of claim 12, wherein the predetermined relationship between fluorescence and concentration of the picolinic acid is linear.

15. The method of claim 12, further comprising the step of:
diluting said sample with water.

16. The method of claim 15 wherein said sample is diluted 1:1000.

17. The method of claim 12, the electromagnetic radiation has a wavelength of from about 250 nanometers to about 290 nanometers to induce fluorescence in the picolinic acid.

18. The method of claim 12, wherein said electromagnetic radiation has a wavelength of about 272 nanometers.

19. The method of claim 12, detecting fluorescence in a spectral range between about 530 nanometers and about 580 nanometers.

20. The method of claim 17, wherein the picolinic acid emits fluorescence in the spectral range of about 545 nanometers.

21. A method of detecting concentration of a target chemical compound in a peracid formulation, comprising:
providing a sample of said peracid formulation;
diluting said sample with water;
adding to said sample an amount of a reducing agent so a peracid and hydrogen peroxide are reduced;
exposing said sample to an electromagnetic radiation at a wavelength to induce fluorescence in the target chemical compound present in the peracid formulation;
detecting the fluorescence emitted by the target chemical compound; and
determining the concentration of the target chemical compound using a predetermined relationship between the fluorescence emitted by and the concentration of the target chemical compound,
wherein the reducing agent neutralizes peracid and hydrogen peroxide in the sample and mitigates effects of the peracid and hydrogen peroxide on the fluorescence detection;
wherein the reducing agent is not an enzyme; and
wherein the peracid formulation comprises a peracid and hydrogen peroxide.

22. The method of claim 19, wherein the target chemical compound is substituted or nonsubstituted mono, di, or tri picolinic acid.

23. The method of claim 22, further comprising the step of adding terbium chloride to said mono, di, or tri picolinic acid in a ratio of about 1:3.

24. The method of claim 21, further comprising the steps of:
pre-determining the amount of water dilution and reducing agent that demonstrate a linear relationship between the emitted fluorescence and the concentration of target chemical compound.

25. The method of claim 21 wherein said diluting is at a ratio of 1:1000 or greater.

26. The method of claim 22 wherein the picolinic acid is dipicolinic acid.

27. The method of claim 22 wherein said dipicolinic acid has the following formula:

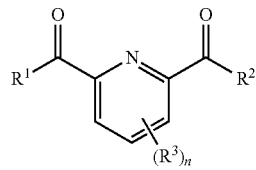

wherein $R^1$ is OH or —$NR^{1a}R^{1b}$, wherein $R^{1a}$ and $R^{1b}$ are independently hydrogen or ($C_1$-$C_6$) alkyl;
$R^2$ is OH or —$NR^{2a}R^{2b}$, wherein $R^{2a}$ and $R^{2b}$ are independently hydrogen or ($C_1$-$C_6$) alkyl;
each $R^3$ is independently ($C_1$-$C_6$)alkyl, ($C_2$-$C_6$)alkenyl or ($C_2$-$C_6$) alkynyl; and
n is a number from zero to 3;
or a salt thereof;
or the following formula:

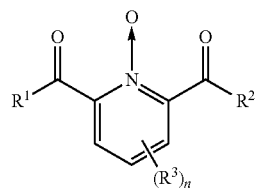

wherein
$R^1$ is OH or —$NR^{1a}R^{1b}$, wherein $R^{1a}$ and $R^{1b}$ are independently hydrogen or ($C_1$-$C_6$) alkyl; $R^2$ is OH or —$NR^{2a}R^{2b}$, wherein $R^{2a}$ and $R^{2b}$ are independently hydrogen or ($C_1$-$C_6$)alkyl; each $R^3$ is independently ($C_1$-$C_6$)alkyl, ($C_2$-$C_6$)alkenyl or ($C_2$-$C_6$)alkynyl; and
n is a number from zero to 3;
or a salt thereof.

\* \* \* \* \*